United States Patent [19]

Roe

[11] Patent Number: 5,428,076
[45] Date of Patent: Jun. 27, 1995

[54] FLEXIBLE, POROUS, ABSORBENT, POLYMERIC MACROSTRUCTURES AND METHODS OF MAKING THE SAME

[75] Inventor: Donald C. Roe, West Chester, Ohio

[73] Assignee: The Procter & Gamble Company, Cincinnati, Ohio

[21] Appl. No.: 317,965

[22] Filed: Oct. 4, 1994

Related U.S. Application Data

[62] Division of Ser. No. 221,327, Mar. 31, 1994, Pat. No. 5,372,766.

[51] Int. Cl.$^6$ .......................... C08J 9/228; C08J 9/232
[52] U.S. Cl. ......................................... 521/53; 521/54; 521/64; 521/88; 521/84.1; 521/141; 521/149; 521/919
[58] Field of Search ...................... 521/53, 54, 64, 149, 521/88, 84.1, 141, 919

[56] References Cited

U.S. PATENT DOCUMENTS

| | | | |
|---|---|---|---|
| Re. 32,649 | 4/1988 | Brandt et al. | 604/368 |
| 3,661,154 | 5/1972 | Torr | 128/284 |
| 3,890,974 | 6/1975 | Kozak | 128/287 |
| 3,901,236 | 8/1975 | Assarsson et al. | 128/284 |
| 3,957,741 | 5/1976 | Rembaum et al. | 526/312 |
| 4,076,663 | 2/1978 | Masuda et al. | 260/17.4 GC |
| 4,076,673 | 2/1978 | Burkholder, Jr. | 260/29.2 EP |
| 4,093,776 | 6/1978 | Aoki et al. | 428/402 |
| 4,117,184 | 9/1978 | Erickson et al. | 428/224 |
| 4,127,944 | 12/1978 | Giacobello | 34/9 |
| 4,132,695 | 1/1979 | Burkholder | 260/29.6 |
| 4,154,898 | 5/1979 | Burkholder | 428/500 |
| 4,190,563 | 2/1980 | Bosley et al. | 260/17.4 GC |
| 4,191,672 | 3/1980 | Salome et al. | 260/29.6 PM |
| 4,269,188 | 5/1981 | Nishizawa | 128/287 |
| 4,282,121 | 8/1981 | Goodrich | 260/17.4 GC |
| 4,286,082 | 8/1981 | Tsubakimoto et al. | 526/240 |
| 4,394,930 | 7/1983 | Korpman | 220/444 |
| 4,410,571 | 10/1983 | Korpman | 427/385.5 |
| 4,413,995 | 11/1983 | Korpman et al. | 604/368 |
| 4,415,388 | 11/1983 | Korpman | 156/78 |
| 4,429,001 | 1/1984 | Kolpin et al. | 428/283 |
| 4,439,385 | 3/1984 | Kuhls et al. | 264/37 |
| 4,446,261 | 5/1984 | Yamasaki et al. | 524/40 |
| 4,497,930 | 2/1985 | Yamasaki et al. | 524/556 |
| 4,541,871 | 9/1985 | Obayashi et al. | 106/197.2 |
| 4,560,372 | 12/1985 | Pieniak | 604/369 |
| 4,587,308 | 5/1986 | Makita et al. | 525/373 |
| 4,625,001 | 11/1986 | Tsubakimoto et al. | 526/88 |
| 4,647,617 | 3/1987 | Satome | 524/733 |
| 4,666,983 | 5/1987 | Tsubakimoto et al. | 526/88 |
| 4,676,784 | 6/1987 | Erdman et al. | 604/368 |
| 4,693,713 | 9/1987 | Chmelir et al. | 604/368 |

(List continued on next page.)

FOREIGN PATENT DOCUMENTS

| | | | |
|---|---|---|---|
| 49944 | 4/1982 | European Pat. Off. | |
| 205674 | 12/1986 | European Pat. Off. | A61L 15/00 |
| 248963 | 12/1987 | European Pat. Off. | C08F 8/32 |
| 303440 | 2/1989 | European Pat. Off. | C08F 20/04 |
| 312952 | 4/1989 | European Pat. Off. | C08F 220/04 |
| 317106 | 5/1989 | European Pat. Off. | C08J 3/06 |
| 318989 | 6/1989 | European Pat. Off. | C08J 3/12 |
| 233014 | 8/1989 | European Pat. Off. | C08F 291/00 |
| 326382 | 8/1989 | European Pat. Off. | C08J 3/12 |
| 349240 | 1/1990 | European Pat. Off. | C08F 2/32 |
| 372981 | 6/1990 | European Pat. Off. | C08F 220/04 |
| 401044 | 6/1990 | European Pat. Off. | C08J 3/24 |
| 293208 | 7/1991 | European Pat. Off. | A61L 15/00 |
| 443627 | 8/1991 | European Pat. Off. | A61F 13/46 |
| 450922 | 9/1991 | European Pat. Off. | C08F 8/14 |
| 450923 | 9/1991 | European Pat. Off. | C08F 8/14 |
| 450924 | 9/1991 | European Pat. Off. | C08F 8/14 |

(List continued on next page.)

OTHER PUBLICATIONS

60/147475 (Eng. abstract WPAT AN 85-226897/37) Aug. 3, 1985 Japan.

(List continued on next page.)

*Primary Examiner*—Morton Foelak
*Attorney, Agent, or Firm*—Loretta J. Henderson; Bart S. Hersko; E. Kelly Linman

[57] ABSTRACT

Flexible, porous, absorbent polymeric macrostructures having flexibility even after extended periods at elevated temperatures and/or low humidities are disclosed. The macrostructure comprises an interparticle crosslinked aggregate and an effective amount of a suitable plasticizer. The macrostructures are suitable for use, for example, in disposable absorbent articles such as diapers.

20 Claims, 4 Drawing Sheets

U.S. PATENT DOCUMENTS

| | | | |
|---|---|---|---|
| 4,734,478 | 3/1988 | Tsubakimoto et al. | 527/300 |
| 4,735,987 | 4/1988 | Morita et al. | 524/436 |
| 4,755,560 | 7/1988 | Ito et al. | 525/100 |
| 4,758,617 | 7/1988 | Tanioku et al. | 524/413 |
| 4,783,510 | 11/1988 | Saotome | 525/329.7 |
| 4,798,861 | 1/1989 | Johnson et al. | 524/458 |
| 4,806,598 | 2/1989 | Morman | 525/63 |
| 4,824,901 | 4/1989 | Alexander et al. | 524/555 |
| 4,826,880 | 5/1989 | Lesniak et al. | 521/53 |
| 4,861,539 | 8/1989 | Allen et al. | 264/204 |
| 5,002,986 | 3/1991 | Fujiura et al. | 524/47 |
| 5,102,597 | 4/1992 | Roe et al. | 264/126 |
| 5,118,719 | 6/1992 | Lind | 521/92 |
| 5,124,188 | 6/1992 | Roe et al. | 428/72 |
| 5,140,076 | 8/1992 | Hatsuda et al. | 525/375 |
| 5,149,334 | 9/1992 | Lahrman et al. | 604/367 |
| 5,149,335 | 9/1992 | Kellenberger et al. | 604/372 |
| 5,154,713 | 10/1992 | Lind | 604/358 |
| 5,171,781 | 12/1992 | Farrar | 524/547 |
| 5,180,622 | 1/1993 | Berg et al. | 428/192 |
| 5,248,709 | 9/1993 | Brehm | 523/221 |
| 5,300,565 | 4/1994 | Berg et al. | 525/54.2 |

FOREIGN PATENT DOCUMENTS

| | | | |
|---|---|---|---|
| 509708 | 10/1992 | European Pat. Off. | C08F 8/14 |
| 522570 | 1/1993 | European Pat. Off. | C08F 2/32 |
| 555692 | 8/1993 | European Pat. Off. | C08J 3/24 |
| 2354184 | 1/1978 | France | B29D 7/02 |
| 62/112655 | 5/1987 | Japan | |
| 63/109897 | 11/1989 | Japan | |
| 94861 | 1/1988 | Taiwan | |
| 1376091 | 12/1974 | United Kingdom | C08J 1/02 |
| 2162525 | 2/1986 | United Kingdom | C08J 3/24 |
| 90/08789 | 8/1990 | WIPO | C08F 265/02 |
| 91/15177 | 10/1991 | WIPO | A61F 13/15 |
| 91/15362 | 10/1991 | WIPO | B32B 3/10 |
| 91/15368 | 10/1991 | WIPO | B32B 31/30 |
| 92/16565 | 10/1992 | WIPO | C08F 2/18 |

OTHER PUBLICATIONS

60/177004 (Eng. abstract) WPAT AN 85–265802/43) Sep. 11, 1985 Japan.

60/255814 (Eng. abstract) WPAT AN 86–033356/05) Dec. 17, 1985 Japan.

62/223203 (Eng. abstract WPAT AN 87–316480/45) Oct. 1, 1987 Japan.

88/023846 (Eng. abstract WPAT AN 89–275123/38) Aug. 14, 1989 Japan.

88/025935 (Eng. abstract WPAT AN 89–273938/38) Aug. 9, 1989 Japan.

1213307 (Eng. abstract WPAT AN 89–289790/40) Aug. 28, 1989 Japan.

2/227435 (Eng. abstract WPAT AN 90-3257249/48) Sep. 10, 1990 Japan.

2,354,184 (Eng. abstract WPAT AN 90542Y/51) Jan. 6, 1978 France.

3,523,617 (Eng. abstract WPAT AN 86–029906/05) Jan. 23, 1986 Germany.

3,741,157 (Eng. abstract WPAT AN 89–179201/25) Jun. 15, 1989 Germany.

3,741,158 (Eng. abstract WPAT AN 89–167033/33) Jun. 7, 1989 Germany.

57/44627 (Eng. abstract WPAT AN 82–32087E/16) Mar. 13, 1982 Japan.

FLEXIBLE, POROUS, ABSORBENT, POLYMERIC MACROSTRUCTURES AND METHODS OF MAKING THE SAME

This is a division of application Ser. No. 08/221,327, filed on Mar. 31, 1994, now U.S. Pat. No. 5,372,766.

FIELD OF THE INVENTION

The present invention relates to absorbent polymeric compositions which, upon contacting liquids such as water or body exudates, swell and imbibe such liquids. More specifically, the present invention relates to polymeric compositions that are macrostructures such as a sheet, film, or strip. Such absorbent polymeric macrostructures are porous so as to be liquid permeable. The macrostructures are flexible and retain their flexibility over extended periods of extreme conditions of elevated temperature and/or low humidity. These flexible, porous, absorbent, polymeric macrostructures are useful by themselves or in absorbent articles such as diapers, adult incontinence pads, sanitary napkins, and the like. The present invention also relates to methods of producing such flexible, porous, absorbent, polymeric macrostructures.

BACKGROUND OF THE INVENTION

Particulate, absorbent, polymeric compositions are capable of absorbing large quantities of liquids such as water and body exudates and which are further capable of retaining such absorbed liquids under moderate pressures. These absorption characteristics of such polymeric compositions make them especially useful for incorporation into absorbent articles such as diapers. For example, U.S. Pat. No. 3,699,103 issued to Harper et al. on Jun. 13, 1972 and U.S. Pat. No. 3,670,731 issued to Harmon on Jun. 20, 1972, both disclose the use of particulate, absorbent, polymeric compositions (also referred to as hydrogels, superabsorbent, or hydrocolloid materials) in absorbent articles.

Conventional particulate, absorbent, polymeric compositions, however, have the limitation that the particles are not immobilized and are free to migrate during processing and/or use. Migration of the particles during processing can lead to material handling losses during manufacturing operations as well as nonhomogeneous incorporation of the particles into structures in which the particles are being used. A more significant problem, though, occurs when these particulate materials migrate during or after swelling. Such mobility leads to high resistance to liquid flow through the material due to the lack of stable interparticle capillary or liquid transport channels. This phenomenon is one form of what is commonly referred to as "gel blocking".

One attempt to overcome the performance limitations associated with particle mobility in the context of their use in absorbent articles has been to immobilize the particulate, absorbent, polymeric compositions by the addition of large quantities of liquid polyhydroxy compounds that act as an adhesive to hold the particles together or to a substrate. An example of this technology is disclosed in U.S. Pat. No. 4,410,571 issued to Korpman on Oct. 18, 1983. While this approach does limit migration before and, to some extent, during swelling, the particles eventually become detached from each other upon presentation of excess liquid to such polymeric compositions, resulting again in the breakdown of any preexisting capillary channels between the particles.

A more recent solution proposed to overcome the problem of absorbent particle mobility is to form these particles into aggregate macrostructures, typically as sheets of bonded absorbent particles. See U.S. Pat. No. 5,102,597 issued to Roe et al. on Apr. 7, 1992. These aggregate macrostructures are prepared by applying an interparticle crosslinking agent to absorbent polymeric precursor particles, physically associating the precursor particles, and reacting the interparticle crosslinking agent with the polymeric material to form interparticle crosslink bonds between the particles. Since under certain conditions the macrostructures can be somewhat inflexible and brittle, a plasticizer can be incorporated into the macrostructure. The plasticizer may be water, high molecular weight hydrophilic organic solvents, or polymeric solutions, or mixtures thereof. See Column 17, line 57 through Column 18, line 15 of Roe et al.

While the macrostructures of Roe et al. are useful in absorbent articles, the specific embodiments taught therein tend to be inflexible as made, or to lose flexibility upon exposure to conditions of high temperature and/or low humidity that may occur under normal storage conditions. For example, absorbent articles are commonly exposed to temperatures of over about 120° F. and/or Relative Humidities of less than about 20% for extended periods in non-climate controlled storage facilities, e.g., for several hours in car trunks or a month or more in a warehouse. As a result, the macrostructures tend to become brittle, crack or otherwise break apart, thereby diminishing the original advantage of immobilizing the absorbent material to improve absorption. The macrostructures also tend to become stiff, thereby decreasing the comfort of the wearer of the absorbent article.

Therefore, it is an object of the present invention to provide a flexible, porous, absorbent, polymeric macrostructure that retains sufficient flexibility under the conditions of high temperature and/or low humidity that may occur under normal storage conditions. It is a further object of the present invention to provide flexible, porous, absorbent polymeric macrostructures that remain intact and transport liquid even upon saturation with excess liquid, even after exposure to such conditions.

It is another object of the present invention to provide a method for producing such flexible, porous, absorbent polymeric macrostructures.

Another object of the present invention is to provide improved absorbent products, absorbent members, and absorbent articles (such as diapers or sanitary napkins)incorporating the flexible, porous, absorbent polymeric macrostructures of the present invention.

SUMMARY OF THE INVENTION

The present invention provides a flexible, porous, absorbent polymeric macrostructure having extended flexibility under extreme conditions of elevated temperature and/or low humidity.

The flexible, porous, absorbent, polymeric macrostructure comprises an interparticle crosslinked aggregate having a circumscribed dry volume greater than about 10.0 mm$^3$. The interparticle crosslinked aggregate comprises a multiplicity of precursor particles of substantially water-insoluble, absorbent, hydrogel-forming, polymer material; and an interparticle crosslinking agent reacted with the polymer material of the precursor particles to form crosslink bonds between different precursor particles. The particulate nature of the precursor particles results in the formation of pores between adjacent precursor particles. The pores are interconnected by intercommunicating channels such that the macrostructure is liquid permeable (i.e., has capillary transport channels).

The macrostructure also comprises a suitable plasticizer, preferably glycerol, in an amount such that the macrostructure has a bending angle at cracking or breaking of at least 90° after being subjected to conditions of 120° F. ±5° F. and 8%±2% Relative Humidity for a period of at least about 4 hours, more preferably at least about 24 hours, most preferably at least about 28 days. In a preferred embodiment, the macrostructure contains at least about 0.45 parts by weight of the plasticizer per one part by weight of the precursor particles of which the interparticle crosslinked aggregate is comprised. The resultant macrostructure has a circumscribed dry volume greater than about 10.0 mm$^3$ and pores that are interconnected by intercommunicating channels such that the macrostructure is liquid permeable.

Due to the interparticle crosslink bonds formed between the precursor particles forming the interparticle crosslinked aggregate, the resultant macrostructure has improved structural integrity, increased liquid acquisition and distribution rates, and minimal gel blocking characteristics. The plasticizer serves to maintain the integrity of the interparticle crosslink bonds such that these properties are retained, even under extreme conditions of elevated temperature and/or low humidity.

The present invention also relates to improved absorbent products, absorbent members, and absorbent articles incorporating the flexible, porous, absorbent, polymeric macrostructures of the present invention.

The present invention also relates to methods of producing such flexible, porous, absorbent, polymeric macrostructures. The interparticle crosslinked aggregate of the macrostructure is produced by applying an interparticle crosslinking agent onto the precursor particles, physically associating the precursor particles into an aggregate, and reacting the interparticle crosslinking agent with the polymer material of the precursor particles while maintaining the physical association to form crosslink bonds between different precursor particles. The interparticle crosslinked aggregate is plasticized by incorporating a plasticizer into the aggregate to impart extended flexibility to the resultant macrostructure even under extreme conditions of elevated temperature and/or humidity. The plasticizing solution can be incorporated into the aggregate during or after its formation.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

1. Introduction

The flexible, porous, absorbent, polymeric macrostructures of the present invention are structures capable of absorbing large quantities of liquids such as water and/or body exudates (e.g., urine or menses) and which are capable of retaining such liquids under moderate pressures. Typically, the macrostructures of the present invention will swell generally isotropically and rapidly absorb the liquids.

As used herein, the term "macrostructure" means a product having a circumscribed volume when substantially dry (i.e., circumscribed dry volume) of at least about 10.0 mm$^3$, preferably at least about 100 mm$^3$, more preferably at least about 500 mm$^3$. Typically, the macrostructures of the present invention will have a circumscribed dry volume much greater than about 500 mm$^3$. In preferred embodiments of the present invention, the macrostructures have a circumscribed dry volume of between about 1000 mm$^3$ and about 100,000 mm$^3$.

While the macrostructures of the present invention may have a number of shapes and sizes, the macrostructures are typically in the form of sheets, films, cylinders, blocks, spheres, fibers, filaments, or other shaped elements. The macrostructures will generally have a thickness or diameter between about 0.25 mm and about 10.0 mm. Preferably for use in absorbent products, the macrostructures are in the form of a sheet. The term "sheet" as used herein describes macrostructures having a thickness greater than about 250 microns. The sheets will preferably have a thickness between about 0.5 mm and about 3 mm, typically about 1 mm.

2. Components of the Macrostructure

A) Interparticle Crosslinked Aggregate

Figure 1:
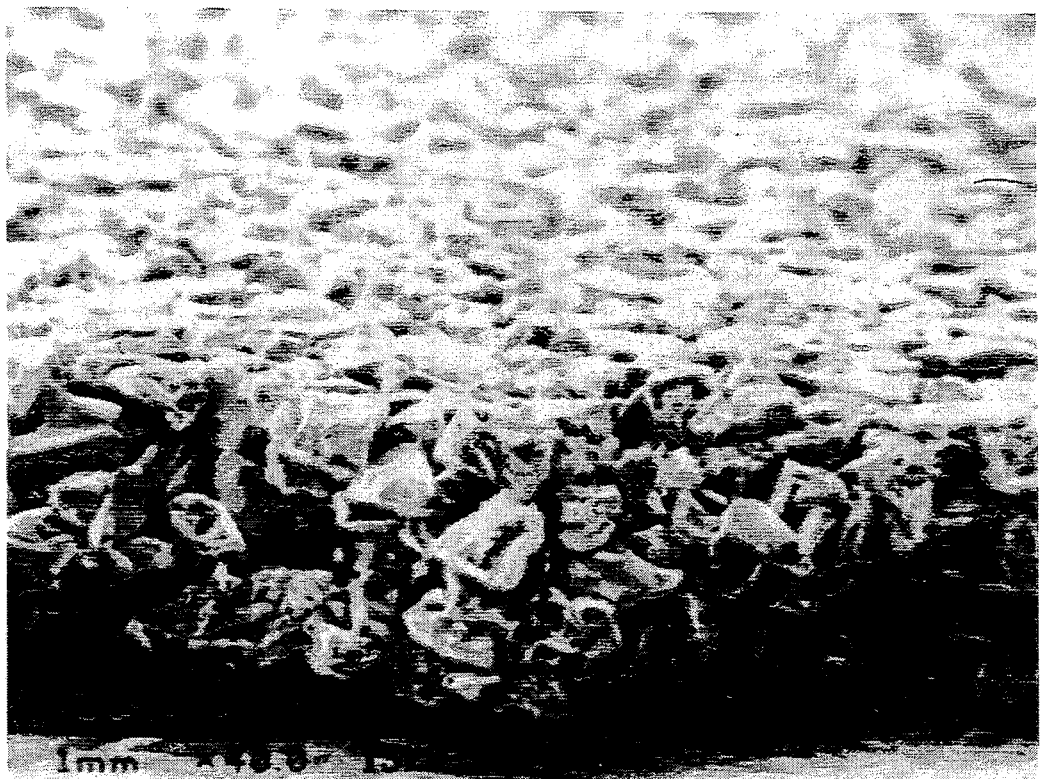
FIG. 1 is a photomicrograph enlarged approximately 40 times showing a perspective view (at 15° from the horizontal) of the edge of an interparticle crosslinked aggregate of which the flexible porous, absorbent, polymeric macrostructure of the present invention is comprised.
Figure 2:
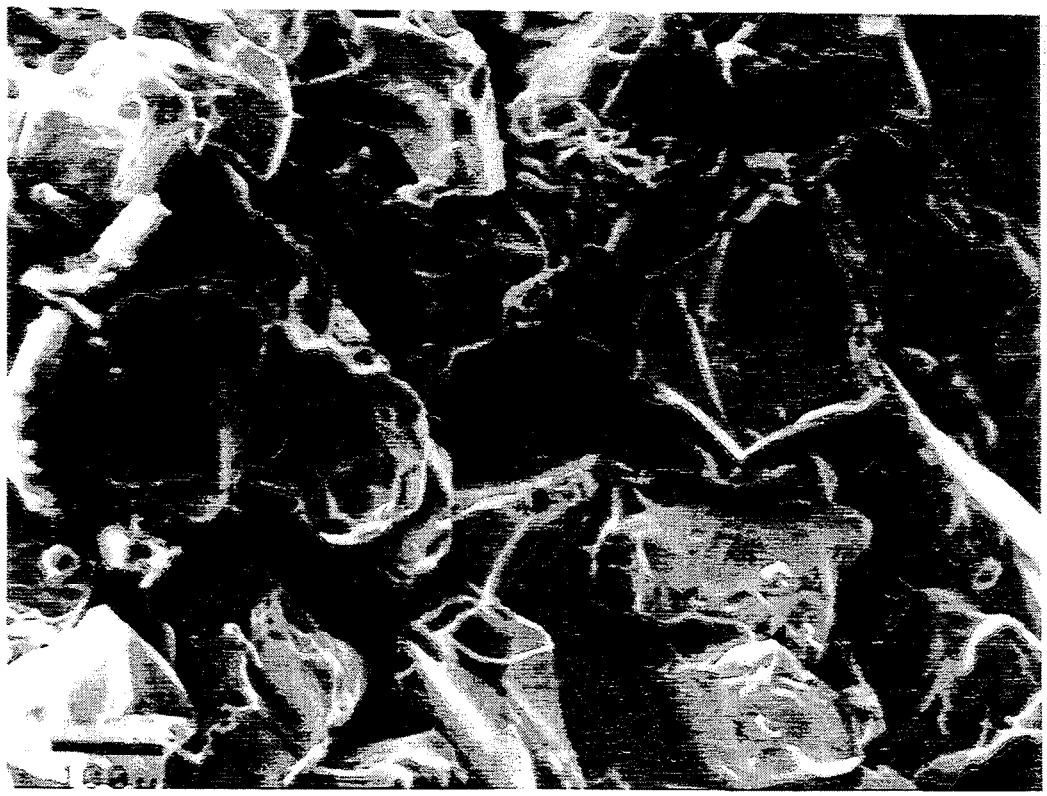
FIG. 2 is a photomicrograph enlarged approximately 120 times of a top view of a portion of the aggregate shown in FIG. 1.
Figure 3:
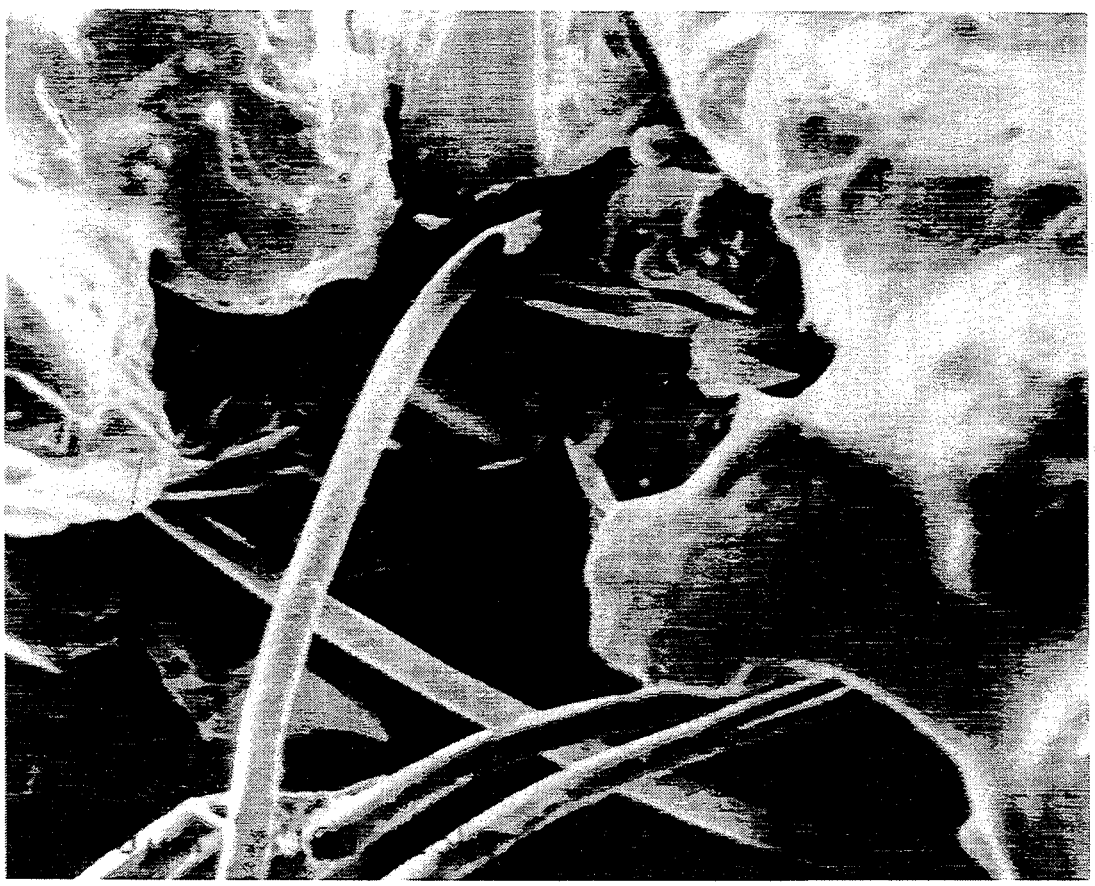
FIG. 3 is a photomicrograph enlarged approximately 100 times of a perspective view (45° from the horizontal) of a portion of an alternative embodiment of an interparticle crosslinked aggregate of the flexible, porous, absorbent, polymeric macrostructure having polyester fibers embedded in the aggregate.

The flexible, porous, absorbent, polymeric macrostructures of the present invention comprise an interparticle crosslinked aggregate such as shown in FIGS. 1–3. Suitable interparticle crosslinked aggregates, including methods of making the same, are described in detail in the above referenced U.S. Pat. No. 5,102,597 to Roe et al; and in commonly assigned U.S. patent application Ser. No. 07/955,635, filed Oct. 2, 1992 in the names of Rezai et al.; the disclosures of which are incorporated herein by reference in their entirety. An interparticle crosslinked aggregate is the porous structure formed by joining together two or more, typically about ten or more in the present invention, previously independent precursor particles. The precursor particles of the interparticle crosslinked aggregate are formed from polymer materials capable of absorbing large quantities of liquids. (Such polymer materials are commonly referred to as hydrogel, hydrocolloid, or superabsorbent materials.) The precursor particles preferably comprise substantially water-insoluble, absorbent, hydrogel-forming, polymer material. Suitable polymer materials will be discussed herein with respect to the polymer materials forming the precursor particles.

The precursor particles are joined together by interparticle crosslinking agents applied thereto and subjected to conditions, while maintaining the physical association of the precursor particles, which are sufficient to react the interparticle crosslinking agent with the polymer material of the precursor particles to form crosslink bonds between the precursor particles that form the interparticle crosslinked aggregate, As shown in FIG. 1, the interparticle crosslinked aggregate is formed from a multiplicity of precursor particles. Due to the preferred size for the precursor particles used herein, the interparticle crosslinked aggregate is typically formed from ten or more, preferably about fifty or more, precursor particles. The precursor particles of the present invention are in the form of discrete units and can comprise granules, pulverulents, spheres, flakes, fibers, aggregates or agglomerates. The precursor particles can have any desired shape. Preferably, as shown in FIGS. 1-2, the precursor particles are in a finely divided powder form of randomly-sized irregular shaped pulverulent granules or flakes.

Although the precursor particles may have a size varying over a wide range, specific particle size distributions and sizes are preferred. For purposes of the present invention, particle size is defined for precursor particles that do not have a large greatest dimension/smallest dimension ratio such as fibers (e.g., granules, flakes, or pulverulents) as the dimension of a precursor particle which is determined by sieve size analysis. Such sieve size analysis is discussed in detail in the above referenced U.S. Pat. No. 5,102,597 to Roe et al..In preferred embodiments of the present invention, the precursor particles will generally range in size from between about 1 micron to about 2000 microns, more preferably between about 20 microns to about 1000 microns.

Further, for purposes of this invention, the mass average particle size of the precursor particles is important in determining the characteristics and properties of the resultant aggregates and thus of the flexible macrostructures. The mass average particle size of a given sample of precursor particles is defined as the particle size which is the average particle size of the sample on a mass basis. A suitable method for determining the mass average particle size of a sample is described in the Test Methods section of the above referenced U.S. Pat. No. 5,102,597 to Roe et al.. The mass average particle size of the precursor particles will generally be from about 20 microns to about 1500 microns, more preferably from about 50 microns to about 1000 microns. In preferred embodiments of the present invention, the precursor particles have a mass average particle size less that about 1000 microns, more preferably less than about 600 microns, most preferably less than about 500 microns. In especially preferred embodiments of the present invention, the mass average particle size of the precursor particles is relatively small (i.e., the precursor particles are fines). In these embodiments, the mass average particle size of the precursor particles is less than about 300 microns, more preferably less than about 180 microns. In an exemplary embodiment, at least about 95% by weight of the precursor particles have a particle size between about 150 microns and about 300 microns. In an alternative embodiment, at least about 95% by weight of the precursor particles have a particle size between about 90 microns and about 180 microns. Narrow precursor particle size distributions are preferred because they result in a higher porosity macrostructure due to their higher void fraction when densified versus broader precursor particle size distributions with equivalent mass average particle sizes.

The particle size of materials having a large greatest dimension/smallest dimension such as fibers is typically defined by their largest dimension. For example, the length of the absorbent fibers is used to define the "particle size". (The denier and/or the diameter of the fibers may also be specified.) In exemplary embodiments of the present invention, the fibers have a length greater than about 5 mm, preferably between about 10 mm and about 100 mm, more preferably between about 10 mm and about 50 mm.

The precursor particles preferably comprise substantially water-insoluble, absorbent, hydrogel-forming, polymer material. Examples of polymer materials suitable for use as the precursor particles herein include those which are prepared from polymerizable, unsaturated, acid-containing monomers such as the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids and mixtures thereof.

Olefinically unsaturated carboxylic acid and carboxylic acid anhydride monomers include the acrylic acids typified by acrylic acid itself, methacrylic acid, ethacrylic acid, alpha-chloroacrylic acid, alpha-cyano acrylic acid, beta-methyl acrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-steryl acrylic acid, itaconic acid, citraconic acid, mesaconic acid, glutaconic acid, aconitic acid, maleic acid, fumaric acid, tricarboxyethylene and maleic acid anhydride.

Preferred polymer materials for use in the present invention possess a carboxyl group. These polymers include hydrolyzed starch-acrylonitrile graft copolymer, partially neutralized starch-acrylonitrile graft copolymer, starch-acrylic acid graft copolymer, partially neutralized starch-acrylic acid graft copolymer, saponified vinyl acetate-acrylic ester copolymers, hydrolyzed acrylonitrile or acrylamide copolymers, slightly network crosslinked products of any of the foregoing copolymers, partially neutralized polyacrylic acid, and slightly network crosslinked products of partially neutralized polyacrylic acid. These polymers may be used either independently or in the form of a mixture of two or more monomers, compounds, or the like. Examples of these polymer materials are disclosed in U.S. Pat. No.

3,661,875; U.S. Pat. No. 4,076,663; U.S. Pat. No. 4,093,776; U.S. Pat. No. 4,666,983; and U.S. Pat. No. 4,734,478; each incorporated herein by reference. Most preferred polymer materials for use as the precursor particles are slightly network crosslinked products of partially neutralized polyacrylic acids and starch derivatives therefrom. Most preferably, the precursor particles comprise from about 50 to about 95%, preferably about 75%, neutralized, slightly network crosslinked, polyacrylic acid (i.e., poly (sodium acrylate/acrylic acid)).

Some non-acid monomers, e.g., the water-soluble or water-dispersible esters of the acid-containing monomers as well as monomers which contain no carboxyl or sulfonic acid groups at all, may also be used to prepare the precursor particles herein. Non-acid monomers are well known materials and are described in greater detail, for example, in U.S. Pat. No. 4,076,663 issued to Masuda et al. on Feb. 28, 1978 and in U.S. Pat. No. 4,062,817 issued to Westerman on Dec. 13, 1977, both incorporated herein by reference.

The individual precursor particles may be formed in any conventional manner. Typical and preferred processes for producing the individual precursor particles are described in U.S. Pat. No. Re. 32,649 reissued to Brandt et al on Apr. 19, 1988; U.S. Pat. No. 4,666,983 issued to Tsubakimoto et al on May 19, 1987; and U.S. Pat. No. 4,625,001 issued to Tsubakimoto et al on Nov. 25, 1986; each incorporated herein by reference. Preferred methods for forming the precursor particles are those that involve aqueous solution or other solution polymerization methods, for example as described in the above-referenced U.S. Pat. No. Re. 32,649. The acid functional groups of the polymer materials formed in the aqueous reaction mixture are also preferably neutralized, e.g., as discussed in the above-referenced U.S. Pat. No. Re. 32,649.

While it is preferred that the precursor particles be manufactured using an aqueous solution polymerization process, it is also possible to carry out the polymerization process using multi-phase polymerization processing techniques such as inverse emulsion polymerization or inverse suspension polymerization procedures, such as described in U.S. Pat. No. 4,340,706 issued to Obaysashi et al. on Jul. 20, 1982; U.S. Pat. No. 4,506,052 issued to Flesher et al. on Mar. 19, 1985; and U.S. Pat. No. 4,735,987 issued to Morita et al. on Apr. 5, 1988; each incorporated herein by reference.

As described above, the precursor particles preferably are polymer materials that are slightly network crosslinked. As recognized in the art, network crosslinking serves to render the precursor particles substantially water-insoluble and in part serves to determine the absorptive capacity and extractable polymer content characteristics of the precursor particles and the resultant aggregate and macrostructure. Exemplary processes for network crosslinking the polymers and typical network crosslinking agents are described in greater detail in the above referenced U.S. Pat. No. 4,076,663.

The individual precursor particles may optionally be surface treated. For example, the particles may be surface treated with a poly-quaternary amine as described in U.S. Pat. No. 4,824,901, Alexander et al., issued Apr. 25, 1989; or preferably surface crosslinked as disclosed in U.S. Pat. No. 4,666,983, Tsubakimoto et al., issued May 19, 1987; and U.S. Pat. No. 4,734,478, Tsubakimoto et al., issued Mar. 29, 1988; each incorporated herein by reference.

Preferred precursor particles of the present invention are those which exhibit a high absorptive capacity so that the resultant aggregate and the flexible macrostructure formed from such precursor particles also have a high absorptive capacity. Absorptive capacity refers to the capacity of a given polymer material to absorb liquids with which it comes into contact. For purposes of this invention, Absorptive Capacity is defined in terms of the amount of Synthetic Urine absorbed by any given polymer material in terms of grams of Synthetic Urine per gram of polymer material. Synthetic Urine is defined, and a suitable procedure for determining Absorptive Capacity is found in the Test Methods section of the above referenced and incorporated U.S. Pat. No. 5,102,597 to Roe et al. Preferred precursor particles of the present invention are those which have an Absorptive Capacity of at least about 20 grams, more preferably at least about 25 grams, of Synthetic Urine per gram of polymer material. Typically, the polymer materials of the precursor particles herein have an Absorptive Capacity of from about 40 grams to about 70 grams of Synthetic Urine per gram of polymer material.

In preferred embodiments of the present invention, the precursor particles used to form the interparticle crosslinked aggregate are substantially dry. The term "substantially dry" is used herein to mean that the precursor particles have a liquid content, typically water or other solution content, less than about 50%, preferably less than about 20%, more preferably less than about 10%, by weight of the precursor particles. In general, the liquid content of the precursor particles is in the range of from about 0.01% to about 5% by weight of the precursor particles. The individual precursor particles can be dried by any conventional method such as by heating. Alternatively, when the precursor particles are formed using an aqueous reaction mixture, water can be removed from the reaction mixture by azeotropic distillation. The polymer-containing aqueous reaction mixture can also be treated with a dewatering solvent such as methanol. Combinations of these drying procedures may also be used. The dewatered mass of polymer material can then be chopped or pulverized to form substantially dry precursor particles of substantially water-insoluble, absorbent, hydrogel-forming, polymer material.

The interparticle crosslinked aggregate of the macrostructure of the present invention also comprises an interparticle crosslinking agent. The interparticle crosslinking agent is applied onto the precursor particles and reacted with the polymer material of the precursor particles while physical association between the precursor particles is maintained. This reaction forms crosslink bonds between the precursor particles. Thus, the crosslink bonds are interparticle in nature (i.e., between different precursor particles). Without wishing to be bound by theory or limit the scope of the invention, it is believed the reaction of the interparticle crosslinking agent with the polymer material of the precursor particles forms crosslink bonds between the polymer chains of different precursor particles (i.e., interparticle crosslink bonds). For the preferred polymers herein, it is believed the interparticle crosslinking agent reacts to form crosslink bonds between the carboxyl groups of the previously independent precursor particles.

For example, and without wishing to be bound by theory or limit the scope of the invention, for the preferred polymer materials possessing carboxyl groups, it is believed that the interparticle crosslinking agent reacts with the carboxyl groups of the polymer materials to form covalent chemical crosslink bonds between the polymer chains of different precursor particles. These covalent chemical crosslink bonds generally arise as a result of the formation of ester, amide, imide or urethane groups by reaction of the functional groups of the crosslinking agents with the carboxyl groups of the polymer material. In preferred executions, it is believed that ester bonds are formed. Thus, preferred interparticle crosslinking agents are those agents capable of reacting with the carboxyl groups in the preferred polymers to form ester bonds.

Interparticle crosslinking agents useful in the present invention are those that react with the polymer material of the precursor particles used to form the interparticle crosslinked aggregates. Suitable interparticle crosslinking agents may comprise a number of different agents such as, for example, compounds having at least two polymerizable double bonds; compounds having at least one polymerizable double bond and at least one functional group reactive with the polymer material; compounds having at least two functional groups reactive with the polymer material; or polyvalent metal compounds. Specific crosslinking agents useful in the present invention are described in more detail in the hereinbefore referenced and incorporated U.S. Pat. No. 4,076,663 and U.S. Pat. No. Re. 32,649; and U.S. patent application Ser. No. 07/955,635, filed on Oct. 2, 1992 in the names of Rezai et al. The interparticle crosslinking agents may also comprise monomers (such as previously described) reactive with the polymer material of the precursor particles to form polymeric crosslink bonds.

Where carboxyl groups are present on or in the polymer material (i.e., the polymer chains) of the precursor particles, preferred interparticle crosslinking agents are solutions possessing at least two functional groups per molecule capable of reacting with the carboxyl group. Exemplary interparticle crosslinking agents include cationic amino-epichlorohydrin adducts such as disclosed in the above referenced U.S. patent application Ser. No. 07/955,635; polyhydric alcohols such as ethylene glycol, diethylene glycol, triethylene glycol, tetraethylene glycol, polyethylene glycol, glycerol (1,2,3-propanetriol), polyglycerol, propylene glycol, 1, 2-propanediol, 1, 3-propanediol, trimethylol propane, diethanolamine, triethanolamine, polyoxypropylene oxyethylene-oxypropylene block copolymer, sorbitan fatty acid esters, polyoxyethylene sorbitan fatty acid esters, pentaerythritol, and sorbitol; polyglycidyl ether compounds such as ethylene glycol diglycidyl ether, polyethylene glycol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether, and propylene glycol diglycidyl ether; polyaziridine compounds such as 2, 2-bishydroxymethyl butanol-tris[3-(i-aziridine) propionate], 1, 6-hexamethyl tolulene diethylene urea, and diphenyl methane-bis-4, 4'-N,N'-diethylene urea; haloepoxy compounds such as epichlorohydrin and a-methylfluorohydrin; polyaldehyde compounds such as glutaraldehyde and glyoxazole, polyamine compounds such as ethylene diamine, diethylene triamine, triethylene tetramine, tetraethylene pentamine, pentaethylene hexamine, and polyethylene imine; and polyisocyanate compounds such as 2, 4-toluene diisocyanate and hexamethylene diisocyanate.

One interparticle crosslinking agent or two or more substantially mutually unreactive interparticle crosslinking agents selected from the group mentioned above may be used.

The proportion of the interparticle crosslinking agent to be used in the present invention is in the range of from about 0.01 parts to about 30 parts by weight, preferably from about 0.5 pans to about 10 parts by weight, most preferably from about 1 part to about 5 pans by weight, per 100 parts by weight of the precursor particles.

In the present invention, other materials or agents can be used with the interparticle crosslinking agent(s) as an aid in producing the interparticle crosslinked aggregate, or in promoting or assisting in the reaction of the interparticle crosslinking agent with the polymer material of the precursor particles, or as associating agents.

For example, water may be used in conjunction with the interparticle crosslinking agent. The water functions to promote uniform dispersion of the interparticle crosslinking agent on the surface of the precursor particles and permeation of the interparticle crosslinking agent into the surface region of the precursor particles. The water also promotes stronger physical association between the precursor particles of the prereacted aggregates, and the dry and swollen integrity of the resultant interparticle crosslinked aggregates. In the present invention, the water is used in a proportion of less than about 20 parts by weight (0 parts to about 20 parts by weight), preferably in the range of from about 0.01 parts to about 20 parts by weight, more preferably in the range of from about 0.1 parts to about 10 parts by weight, based on 100 parts by weight of the precursor particles. The actual amount of water to be used will vary depending upon the kind of polymer material and the particle size of the precursor particles.

Organic solvents may also be used in conjunction with the interparticle crosslinking agent. The organic solvents are used to promote uniform dispersion of the interparticle crosslinking agent on the surface of the precursor particles. The organic solvents are preferably hydrophilic organic solvents. The hydrophilic organic solvents useful in the present invention include lower alcohols such as methanol, ethanol, n-propanol, isopropanol, n-butanol, isobutanol, sec-butanol and t-butanol; ketones such as acetone, methylethyl ketone, and methylisobutyl ketone; ethers such as dioxane, tetrahydrofuran, and diethyl ether; amides such as N, N'-dimethylformamide and N,N'-diethylformamide; and sulfoxides such as dimethyl sulfoxide. The hydrophilic organic solvent is used in the present invention in a proportion of less than about 60 parts by weight (0 parts to about 60 pads by weight), preferably in the range of from about 0.01 pads to about 60 parts by weight, more preferably from about 1 part to about 20 parts by weight, based on 100 parts by weight of the precursor particles. The actual amount of hydrophilic organic solvent to be used will vary depending upon the kind of polymer material and the particle size of the precursor particles.

The interparticle crosslinking agent may also be used in a mixture with water and one or more hydrophilic organic solvents. It has been found that the use of a water/interparticle crosslinking agent solution provides the greatest penetration of the crosslinker into the surface region of the precursor particles, while a solution of hydrophilic organic solvent/interparticle crosslinking agent provides minimal penetration of the crosslinker. However, a mixture of all three agents is preferred in order to control the amount of the penetration of the interparticle crosslinking agent into the surface region of the precursor particles. Specifically, it has been found that the higher the water to organic solvent component ratio, the deeper the crosslinker penetration, the greater the fluid stability of the macrostructure under stress, and the greater the reduction in the resultant absorptive capacity of the macrostructure. Typically, the ratio of water to hydrophilic organic solvent in the solution will be in the range of from about 10:1 to about 1:10. The hydrophilic organic solvent/water/interparticle crosslinking agent solution is used in a proportion less than about 60 parts by weight (0 parts to about 60 parts by weight), preferably in the range of from about 0.01 parts to about 60 parts by weight, more preferably from about 1 part to about 20 parts by weight, based on 100 parts by weight of the precursor particles.

Other optional components may also be mixed with the solution containing the interparticle crosslinking agent. For example, an initiator, a catalyst, or non-acid co-monomer materials may be added. Examples of these materials suitable for use herein are described in the above referenced U.S. Pat. No. Re. 32,649.

The method of producing the interparticle crosslinked aggregate comprises the steps of providing precursor particles of the type herein described; applying an interparticle crosslinking agent to a portion of the precursor particles; physically associating the precursor particles to form an aggregate; shaping the aggregate; and reacting the interparticle crosslinking agent with the polymer material of the precursor particles of the aggregate, while maintaining the physical association of the precursor particles, to form crosslink bonds between the polymer chains of different precursor particles.

The interparticle crosslinking agent may be applied onto the precursor particles by any of various techniques and apparatus used for applying solutions to materials including coating, dumping, pouring, dropping, spraying, atomizing, condensing, or immersing the interparticle crosslinking agent onto the precursor particles. As used herein, the term "applied onto" means that at least a portion of the surface area of at least one of the precursor particles to be joined has the interparticle crosslinking agent on it. Preferably, the interparticle crosslinking agent is coated onto the entire surface of most, preferably all, of the precursor particles so as to enhance the efficiency, strength, and density of the interparticle crosslink bonds between the precursor particles.

In a preferred embodiment of the present invention, the interparticle crosslinking agent is applied to a layer(s) of the precursor particles by spraying the layer(s) with an amount of a mixture comprising water and the interparticle crosslinking agent sufficient to cause effective crosslinking, such as described in detail in the commonly assigned U.S. patent application Ser. No. 07/955,638 filed Oct. 2, 1992 in the names of Kolodesh et al., which is incorporated herein by reference.

In an alternative embodiment of the present invention, after the interparticle crosslinking agent has been applied onto the precursor particles, the interparticle crosslinking agent is mixed with the precursor particles by any of a number of mixing techniques to insure that the precursor particles are thoroughly coated with the interparticle crosslinking agent to thereby enhance the efficiency, strength, and density of the crosslink bonds between the precursor particles. The mixing can be accomplished using various techniques and apparatus, including various mixers or kneaders, as are known in the art.

Before, during, or after applying the interparticle crosslinking agent onto the precursor particles, the precursor particles are physically associated together to form an aggregate macrostructure. The term "physically associated" is used herein to mean that the precursor particles are brought together and remain in contact with each other as component parts in any of a number of various ways and spatial relationships so as to form a single unit (an aggregate macrostructure).

The precursor particles are preferably physically associated together by applying an associating agent onto the precursor particles and physically contacting the precursor particles at at least the portion of the surface of the precursor particles having the associating agent applied thereto. Preferred associating agents cause the polymer material of the precursor particles, when brought together, to adhere together by the action of fluid surface tension forces and/or the entanglement of polymer chains due to external swelling. Associating agents useful in the present invention include hydrophilic organic solvents, typically low molecular weight alcohols such as methanol, ethanol, or isopropanol; water; a mixture of hydrophilic organic solvents and water; certain interparticle crosslinking agents as hereinbefore described; volatile hydrophobic organic compounds such as hexane, octane, benzene or toluene; or mixtures thereof. Preferred associating agents are water, methanol, isopropanol, ethanol, interparticle crosslinking agents such as glycerol, or mixtures thereof. Typically the associating agent comprises a mixture including an interparticle crosslinking agent such that the step of applying an interparticle crosslinking agent is carried out simultaneously with the step of applying an associating agent.

The associating agents may be applied to the precursor particles by any of various techniques and apparatus used for applying solutions to materials including coating, dumping, pouring, spraying, atomizing, condensing, or immersing the associating agent on the precursor particles. The associating agent is applied onto at least a portion of the surface area of at least one of the precursor particles to be joined per aggregate. Preferably, the associating agent is coated onto the entire surface of most, preferably all, of the precursor particles. In a preferred embodiment, the associating agent is applied by spraying a layer(s) of the precursor particles with the associating agent as described in the above referenced and incorporated U.S. patent application Ser. No. 07/955,638 filed in the names of Kolodesh et al. Alternatively, the associating agent can be mixed with the precursor particles by any of a number of mixing techniques and mixing apparatus to insure that the precursor particles are thoroughly coated with the associating agent.

When an associating agent has been applied to the precursor particles, the precursor particles may be physically contacted together in a number of different ways. For example, the associating agent alone may hold the particles together in contact. Alternatively, gravitational forces may be used to insure contact between the precursor particles. Further, the particles may be placed in a container having a fixed volume so as to insure contact between the precursor particles.

The precursor particles can alternatively be physically associated together by physically constraining the precursor particles such that they are in contact with each other. For example, the precursor particles may be packed tightly into a container having a fixed volume such that the precursor particles physically contact each other. Alternatively or in combination with the above procedure, gravitational forces may be used to physically associate the precursor particles. The precursor particles may also be physically associated together via electrostatic attraction or by the introduction of an adhering agent (e.g., an adhesive material such as a water-soluble adhesive) to adhere them together. The precursor particles may also be attached to a third member (a substrate) such that the precursor particles are brought into contact with each other by the substrate.

In an alternative and preferred step in forming the interparticle crosslinked aggregate, the aggregate of the precursor particles is shaped into various geometries, spatial relationships, and densities to form an aggregate having a defined shape, size, and/or density. The aggregate may be shaped by any conventional shaping techniques as are known in the art, such as casting, molding, or forming operations, or a combination thereof. Any suitable apparatus as are known in the art may be used to carry out such operations, and the operation may be performed with the material or portions of the apparatus either hot and/or cold.

In a preferred embodiment, the dry precursor particles are continuously layered so as to substantially cover a predetermined area of a support means; the layer(s) is then sprayed with an amount of a mixture comprising water and the interparticle crosslinking agent sufficient to cause effective crosslinking; pressure is applied to form a sheet; and the sheet is cured, i.e., the interparticle crosslinking reaction is caused. Such a method is described in detail in the above referenced and incorporated U.S. patent application Ser. No. 07/955,638 filed Oct. 2, 1992 in the names of Kolodesh et al.

In an alternative embodiment of the present invention an aggregate mixture of precursor particles, an interparticle crosslinking agent, water, and a hydrophilic organic solvent are mixed and extruded in a conventional extruder apparatus to feed a pair of driven compaction rolls having a fixed (but variable) gap between the rolls so as to compress the aggregate into the form of a sheet. The sheet is then processed to specific lengths to provide macrostructures that have a specifically designed size, shape, and/or density. Such a method is described in detail in the above referenced U.S. Pat. No. 5,102,597 to Roe et al.

Simultaneously or after the interparticle crosslinking agent has been applied, the precursor particles have been physically associated together to form an aggregate, and the aggregate has been shaped, the interparticle crosslinking agent is reacted with the polymer material of the precursor particles of the aggregate, while maintaining the physical association of the precursor particles, to form crosslink bonds between the precursor particles to form an interparticle crosslinked aggregate macrostructure.

The reaction between the interparticle crosslinking agent and the polymer material must be activated and completed to form the crosslink bonds between different precursor particles to form the interparticle crosslinked aggregate. The method for activating and completing the reaction depends on the type of precursor material used and the composition of the interparticle crosslinking agent and any optional components (including a plasticizer when the macrostructure is to be flexibilized during formation of the interparticle crosslinked aggregate). In general, the reaction may be caused by irradiation (e.g., ultraviolet, gamma- or X-radiation), by a catalyst as an initiator and an activator, or by thermal activation (heating) using any of a number of different apparatus as are known including the various ovens or driers as are known.

Where it is desired to plasticize the aggregate during the formation of the aggregate as described herein below, the precursor particles, interparticle crosslinking agent, and plasticizer are selected such that the interparticle crosslinking agent has a lower activation energy than that of the plasticizer with the precursor particles. A method is then selected which will activate the reaction of the interparticle crosslinking agent but not the plasticizer with the polymeric precursor particle material to form the interparticle crosslink bonds. In general, such reaction is caused by supplying heat or other forms of energy, e.g., ultraviolet or infrared radiation, sufficient to cause the interparticle crosslinking agent to react, but insufficient for reaction of the plasticizer. Supplying excessive energy may cause the plasticizer to react with the polymeric material of the precursor particles and/or be driven off due to its volatility, thus necessitating an additional step to plasticize the resulting interparticle crosslinked aggregate. Preferential reaction of the interparticle crosslinking agent can be caused, for example, by using a crosslinking agent which reacts with the polymer at ambient room temperature (about 18°–35° C., preferably about 18°–25° C.) while the plasticizer does not appreciably react at this temperature. For interparticle crosslinking agents requiring above ambient temperatures for activation, such preferential reaction can be caused by heating to a temperature which activates the crosslinking agent but which does not activate the plasticizer. In general, for a plasticizer comprising a water-soluble polyhydroxy compound described herein, this will involve heating to a temperature of less than about 150°, preferably less than about 140°, more preferably less than about 130° C., most preferably less than about 100° C., generally for a period of less than about 60 minutes. Alternatively, preferential reaction of the interparticle crosslinking agent without reaction of the plasticizer may be caused by using ultraviolet radiation in the presence of a suitable initiator.

The reaction usually involves subjecting the physically associated particles to a predetermined temperature for a predetermined amount of time. Heating activates and drives the reaction and drives of any volatiles that may be present. The reaction conditions will generally involve heating the associated precursor particles and the interparticle crosslinking agent at a sufficient temperature for a sufficient time to complete the interparticle crosslinking reaction. The crosslinking reaction can be promoted by adding an initiator and/or a catalyst to the interparticle crosslinking agent to reduce the time and/or the temperature and/or the amount of interparticle crosslinking agent required to join the precursor particles together. Generally, however, the reaction is conducted in the absence of a catalyst. The actual time and temperatures used will vary depending upon the specific polymer materials used for the precursor particles, the specific interparticle crosslinking agents used, the presence or absence of a plasticizer in the reaction step, the presence or absence of a catalyst used to drive the reaction, and the thickness or diameter of the macrostructure. Specific reaction steps involved for various interparticle crosslinking agents is discussed below in conjunction with the specific chemical structure of the interparticle crosslinking agent or a mixture containing the same.

If a cationic amino-epichlorohydrin adduct is used as the cross-linking agent, as is described the the above referenced and incorporated U.S. patent application Ser. No. 07/955,635 filed on Oct. 2, 1992 in the names of Rezai et al.; the relatively reactive cationic functional groups of the adduct causes the crosslinking reaction with the polymer material of the precursor particles to occur at relatively low temperatures. Indeed, this crosslinking reaction can occur at ambient room temperatures. Such ambient temperature curing is particularly desirable when the interparticle crosslinking agent is in a mixture containing a plasticizer as described herein. Ambient curing is typically carried out at a temperature of from about 18° C. to about 35° C. for from about 12 to about 48 hours, preferably from about 18° to about 25° C. for from about 24 to 48 hours. Alternatively, the crosslinking reaction between such cationic amino-epichlorohydrin adducts and the polymeric material of the precursor particles can be carried out at elevated temperatures to speed up the reaction as described in the above referenced U.S. patent application Ser. No. 07/955,635.

If a non-ionic crosslinking agent, such as glycerol, is to be used, as is described in the above incorporated U.S. Pat. No. 5,102,597 issued to Roe et al., the interparticle crosslinking reaction is typically caused by heating, generally to a temperature above about 90° C., for a sufficient time to complete the crosslinking reaction. Typically, the reaction will generally be carried out at a temperature in the range from about 120° C. to about 300° C., more preferably from about 150° C. to about 250° C. The time to complete the reaction, in the absence of catalysts, will generally be from about 5 minutes to about 6 hours, more preferably from about 10 minutes to about 4 hours. For the preferred polymer material of the precursor particles, slightly network crosslinked products of partially neutralized polyacrylic acid, and an interparticle crosslinking agent such as glycerol or trimethylol propane, such reaction conditions will involve a temperature of from about 170° C. to about 220° C. for about 3 hours to about 30 minutes, respectively. More preferably, the reaction is carried out at a temperature between about 190° C. to about 210° C. for about 5 minutes to about 45 minutes, respectively.

Ultraviolet radiation may be used to activate the interparticle crosslinking reaction where the interparticle crosslinking agent comprises a compound having at least one polymerizable double bond and which is reactive with the precursor particle, for example, a compound having at least two polymerizable double bonds or a compound having at least one polymerizable double bond and at least one functional group reactive with the polymer material. Suitable interparticle crosslinking agents include acrylic acid or oligomers thereof containing a polymerizable double bond. Ultraviolet radiation polymerization methods as are known in the art are suitable for use herein.

The physical association of the precursor particles needs to be maintained during the reaction step so that sufficient interparticle crosslink bonds are formed. If forces or stresses sufficient to dissociate the precursor particles are present during the reaction step, the crosslink bonds between the precursor particles (interparticle crosslink bonds) may not be formed. The physical association of the precursor particles is typically maintained by insuring minimal dissociation forces or stresses are introduced during the reaction step.

As an optional and preferred step in the method of forming the interparticle crosslinked aggregate, the component precursor particles are surface treated as described herein above. Preferably, the interparticle crosslinking agent applied to the precursor particles also serves as the surface crosslinking agent such that the interparticle crosslinked aggregate is preferably simultaneously formed and surface crosslinked.

As previously discussed, the steps in the method for producing the interparticle crosslinked aggregate need not be carried out in any specific order and may be carried out simultaneously. For example, a simultaneous method is described in detail in the above referenced U.S. Pat. No. 5,102,597 to Roe et al. By this method, the interparticle crosslinking agent is applied simultaneously with the physical association of the precursor particles, the mixture is subsequently shaped into a preferred shape and typically a desired density, and the interparticle crosslinking agent is subsequently reacted with the polymer material of the precursor particles, either immediately after the above steps are completed or after the aggregate has been left standing for a period of time, to simultaneously form and surface crosslink the interparticle crosslinked aggregate. Another method is described in the above referenced and incorporated U.S. patent application Ser. No. 07/955,638 filed in the names of Kolodesh et al.

As shown in FIGS. 1–2 the resultant interparticle crosslinked aggregate has pores (the dark areas of the photomicrograph) between adjacent precursor particles. These pores are maintained in the flexible macrostructure comprising the interparticle crosslinked aggregate. The pores are small interstices between adjacent precursor particles that allow the passage of liquid into the interior of the aggregate and the macrostructure formed therefrom. The pores are formed into the aggregate because the precursor particles do not "fit" or pack tightly enough, even when compressed, to eliminate the pores. (The packing efficiency of the precursor particles is less than 1.) The pores are generally smaller than the constituent precursor particles and provide capillaries between the precursor particles to transport liquid into the interior of the macrostructure.

The pores are interconnected with each other by intercommunicating channels between the pores. The channels allow liquids contacting the macrostructure to be transported via capillary forces (i.e., capillary channels are formed) to other portions of the macrostructure so that the total volume of the macrostructure is used in absorbing such liquids. Further, when swollen, the pores and the intercommunicating channels allow liquids to pass through the macrostructure either to layers of precursor particles remote from the initial point of liquid contact or to other structures in contact with the macrostructure. Thus, the macrostructure is considered to be liquid permeable due to the pores and the intercommunicating channels.

The void fraction (i.e., the total volume of the macrostructure that comprises the pores and the channels) has a minimum value for a given precursor particle size distribution. In general, the narrower the precursor particle size distribution, the higher the void fraction will be. Thus, it is preferred, so as to provide higher void fractions in a densified state, that the precursor particles have a relatively narrow particle size distribution.

Another feature of the interparticle crosslinked aggregate and the flexible macrostructures of the present invention is that the aggregate/macrostructures swell generally isotropically, even under moderate confining pressures, when liquids are deposited onto or come into contact therewith. Isotropic swelling is used herein to mean that the aggregate/macrostructure swells generally equally in all directions when wetted. Isotropic swelling is an important property of the macrostructure because the precursor particles and the pores are able to maintain their relative geometry and spatial relationships even when swollen such that the existing capillary channels are maintained, if not enlarged, during use. (The pores and the precursor particles get larger during swelling.) Thus, the macrostructure can imbibe and/or transport through itself additional loadings of liquid while not gel blocking.

An indication that crosslink bonds are being formed in the interparticle crosslinked aggregate between the previously independent precursor particles is that the resultant aggregate macrostructures (including a flexible macrostructure thereof) are fluid (i.e., liquid) stable. "Fluid stable" is used herein to mean a macrostructure comprising an interparticle crosslinked aggregate that upon contact with or swelling (with and/or without stress) in an aqueous fluid remains substantially intact (i.e., most of the previously independent component precursor particles remain joined together). While the definition of fluid stability recognizes that most of the precursor particles remain joined together, preferably all of the precursor particles used to make up the interparticle crosslinked aggregate remain joined together. However, it should be recognized that some of the precursor particles may dissociate themselves from the aggregate if, for example, other particles have been subsequently water agglomerated to the aggregate.

Fluid stability is an important feature of the interparticle crosslinked aggregate and of the flexible macrostructures of the present invention because it allows the aggregate/macrostructure to maintain its relative structure in both the dry and swollen states, and because it immobilizes component precursor particles. In an end product such as an absorbent member or an absorbent article, fluid stability is beneficial in reducing gel blocking since precursor particles remain aggregated even when contacted with liquid, and allows one to use previously independent fine particles in an aggregate form to increase the rate of fluid uptake of the resultant macrostructure without introducing the element of gel blocking.

Fluid stability can be measured in an aggregate macrostructure by a two step process. The initial dynamic response of the aggregate macrostructure upon contact with the aqueous fluid is observed and then the fully swollen equilibrium condition of the aggregate macrostructure is observed. A test method for determining fluid stability based on these criteria is described in the Test Methods section of the above referenced U.S. Pat. No. 5,102,597 to Roe et al.

FIG. 3 shows an alternative embodiment of an interparticle crosslinked aggregate wherein reinforcing members such as fibers (fibrous or fiber material) are embedded in the aggregate. The reinforcing members provide strength (i.e., structural integrity) to the swollen macrostructure. In certain embodiments, the reinforcing fibers also provide members that quickly wick liquids to other portions of the macrostructure and/or additional absorbent material. The reinforcing members preferably comprise fibers (also referred to as reinforcing fibers); although other materials such as filaments, coils, webs, nonwoven webs, woven webs, or scrims as are known for their reinforcing properites may be used. FIG. 3 shows an embodiment wherein polyester fibers are interwoven throughout the aggregate. Specifically, the polyester fibers are contained within the intercommunicating channels to provide increased swollen structural integrity for the macrostructure. Various types of fiber material can be used for the reinforcing members in the aggregate. Any type of fiber material which is suitable for use in conventional absorbent products is also suitable for use in the aggregate. The use of reinforcing fibers, including methods of incorporation into the aggregate and specific examples of suitable fibers, is described in detail in the above referenced U.S. Pat. No. 5,102,597 to Roe et al.

B) The Plasticizer

The macrostructure also comprises a plasticizer which imparts extended flexibility to the macrostructure under extreme environmental conditions of elevated temperature and/or low humidity. Disposable absorbent articles may often be subjected during storage to temperatures of over about 120° F. and/or relative humidities of less than about 20% for extended periods, e.g., from about several hours to over one or more months in non-climate controlled storage facilities such as certain warehouses and car trunks. As a result, interparticle crosslinked aggregates that are incorporated into the article and that are not flexibilized in accordance with the present invention tend to crack or break such that the absorption benefits of the aggregate are diminished. In addition, the interparticle crosslinked aggregates that are not flexibilized in accordance with the present invention tend to be or become stiff thereby diminishing the comfort of the wearer of the absorbent article.

The macrostructure preferably comprises a suitable plasticizer in an amount such that the macrostructure has a bending angle at cracking or breaking of at least 90° after being subjected to conditions of 120° F.±5° F. and 8%±2% Relative Humidity for at least about 4 hours, more preferably at least about 24 hours, most preferably at least about 28 days. In a preferred embodiment, the macrostructure contains at least about 0.45 parts by weight of the plasticizer, more preferably at least about 0.50 parts by weight of the plasticizer, most preferably at least about 0.60 parts by weight of the plasticizer, per part by weight of the precursor particles of which the interparticle crosslinked aggregate is comprised.

Effective plasticization in accordance with the present invention is influenced by the water/plasticizer concentration in the solution used to plasticize the macrostructure, the chemical nature of the plasticizer, the time allowed to plasticize the macrostructure, and the thickness of the macrostructure being plasticized.

The plasticizer is characterized by having a boiling point that is sufficiently high to minimize its vaporization over long periods under the above storage conditions, preferably greater than 125° C., more preferably greater than about 150° C., even more preferably greater than about 175° C., most preferably greater than about 250° C. The plasticizer preferably also has a molecular size that enables its penetration into the interparticle crosslinked aggregate at least with the assistance of water. In addition, the plasticizer is preferably sufficiently hydrophilic so as to be water-soluble and to have affinity for the gel that is formed when an aqueous plasticizer solution is applied to the precursor particles or the interparticle crosslinked aggregate as described herein. The hydrophilicity of the plasticizer tends to increase with the number of hydrophilic groups, such as hydroxyl groups, in the plasticizer. In contrast, plasticizers possessing hydrophobic groups such as methyl groups tend to have less water-solubility and gel affinity. Without intending to be bound by theory or limit the scope of the invention, it is believed that the presence of such hydrophobic groups results in slower and/or reduced penetration of such a plasticizer into the aggregate such that extended flexibility is not, at least not readily in terms of commercial processing, achieved or maximized. It is also believed that a plasticizer having a relatively even distribution of hydrophilic groups, more preferably such a plasticizer also having a relatively compact molecular structure with such an even distribution of hydrophilic groups (e.g., glycerol) has higher hydrophilicity and gel affinity and thus tends to provide better plasticization. The plasticizer is preferably a water-soluble polyhydroxy compound. Suitable water-soluble polyhydroxy compounds include glycerol; 1,2-propane diol; 1,3-propanediol; ethylene glycol; sorbitol; sucrose; polymeric solutions such as those including polyvinyl alcohol, ester precursors of polyvinyl alcohol, or polyethylene glycol; polyglycerols having a weight average molecular weight of from about 150 to about 800; polyoxyethylene glycols (e.g., PEG-400, a polyoxyethylene glycol having a weight average molecular weight of about 400 and commerically available from the Union Carbide Company of Danbury, Conn.) and polyoxypropylene glycols having a weight average molecular weight of from about 200 to about 400, preferably from about 200 to about 100, most preferably from about 200 to about 600; or mixtures of any of the foregoing. The plasticizer is preferably selected from glycerol, ethylene glycol, 1,2-propane diol; 1,3-propanediol, and mixtures thereof, more preferably glycerol or a mixture of glycerol and one of these other plasticizers, most preferably glycerol.

The plasticization step can be done simultaneous with (i.e., in situ) or after formation of the interparticle crosslinked aggregate. Plasticization of the aggregate during its formation is preferably achieved by applying the plasticizer in admixture with the interparticle crosslinking agent, more preferably also in admixture with water (i.e., an aqueous plasticizing solution containing the interparticle crosslinking agent), to the associated precursor particles. Alternatively, the plasticizer or a mixture of water and the plasticizer (i.e., an aqueous plasticizing solution) can be so applied in a separate step from that of applying the interparticle crosslinking agent. As will be understood by the skilled artisan, the plasticizing solution may contain the interparticle crosslinking agent, associating agent, and/or other optional components previously described in reference to materials or agents used with the interparticle crosslinking agent.

For in situ plasticization, the interparticle crosslinking agent, plasticizer, and reaction method are selected as previously described so as to react the interparticle crosslinking agent, but not the plasticizer, with the polymeric material of the precursor particles. The plasticizer is thereby entrapped in the interparticle crosslink bond structures during the crosslinking reaction. Preferred examples of plasticizing an interparticle crosslinking agent during its formation are described in the above referenced U.S. patent application Ser. No. 07/955,635, filed Oct. 2, 1992, in the names of Rezai et al.

Alternatively, the plasticizer is added to the aggregate after its formation, preferably by applying a plasticizing solution comprising water and the plasticizer to the aggregate (i.e., applying an aqueous plasticizing solution).

Whatever the method of application of the plasticizer and whether the plasticization is being performed in situ or after formation of the interparticle crosslinked aggregate, the amount of plasticizer, or the concentration of plasticizer in a solution and the amount of solution, that is applied to the precursor particles is preferably selected such that the resultant macrostructure will contain at least about 0.45 parts, more preferably at least about 0.50 parts, most preferably at least about 0.60 parts of plasticizer by weight per 1 part by weight of the precursor particles making up the interparticle crosslinked aggregate. Generally, up to about 1 part by weight of plasticizer per 1 part by weight of the precursor particles is used. Higher levels of plasticizer may be used. However, the resultant flexible macrostructure tends to become gummy with increasing levels of plasticizer over about 1 part by weight per 1 part by weight precursor particles.

Whether the plasticization is carried out during or after formation of the aggregate, it is preferred that water be present in the plasticizing solution in order to facilitate penetration (i.e., penetration occurs more quickly or deeply) of the plasticizer into the interparticle crosslinked aggregate. Without intending to be bound by theory or limit the scope of the invention, it is believed that an appropriate balance of water/plasticizer provides a sufficient solubility and thus diffusion rate of the solution in the interparticle crosslinked aggregate such that the plasticizer reaches the vicinity of the interparticle crosslink bonds, preferably substantially surrounding substantially all of the crosslink bonds, in an efficient manner. In addition, the water causes swelling of the polymeric material of the precursor particles thereby enhancing penetration of the plasticizer therein. The solubility of the solution in the aggregate tends to increase with an increasing water concentration. However, as the water concentration increases, the plasticizer concentration in the vicinity of the interparticle crosslink bonds tends to decrease (although the total amount of plasticizer is unchanged). (This is one reason that an aqueous solution of plasticizer is preferred, rather than a multistep method wherein the first step is the application of water followed by application of plasticizer.) In other words, the solubility and diffusion rate of the solution in the aggregate tends to decrease with an increasing solution plasticizer concentration such that a higher concentration of plasticizer would remain in the interparticle bond area to thereby provide better plasticization efficiency.

However, too much plasticizer in the solution may hinder penetration into the interparticle crosslinked aggregate.

The plasticizing solution preferably contains at least about 50 weight %, more preferably at least about 60 weight %, most preferably at least about 60–80 weight %, plasticizer, and less than about 50 weight %, more preferably less than about 40 weight %, most preferably from about 20–40 weight % water based on the total weight of the plasticizer and water in the solution. Relative plasticizer concentrations greater than about 80 weight % may be used but may not sufficiently penetrate the interparticle crosslinked aggregate in a time efficient manner. In general, higher plasticizer concentrations may be used where the plasticizer is being incorporated during formation of the interparticle crosslinked aggregate than after formation thereof, since in the former method the plasticizer tends to be present in the vicinity of the interparticle bonds as they form.

For plasticization during formation of the interparticle crosslinked aggregate, the plasticizing solution is applied to the physically associated particles as previously described in reference to application of the interparticle crosslinking agent. The interparticle crosslinking agent is then reacted as previously described without reacting the plasticizer to form the flexible, porous, absorbent polymeric macrostructure.

For plasticization of a pre-formed interparticle crosslinked aggregate, the plasticizing solution can be applied to the aggregate in a number of different ways including spraying, coating, atomizing, immersing, or dumping the solution onto the aggregate. The application is preferably in the amount of about 0.6 g to about 1.5 g of plasticizing solution per gram of the non-plasticized interparticle crosslinked aggregate. Application ratios greater than about 1.5 g solution per gram of aggregate may require longer solution penetration times as described below, or result in pooling of the solution on the aggregate surface. If desired, any excess solution can be recycled or otherwise removed.

For either method, sufficient time is preferably allowed to enable the plasticizing solution to penetrate at least the surface of the precursor particles of the physically associated aggregate or the interparticle crosslinked aggregate throughout at least substantially all of the portion of the particles which will react with the interparticle crosslinking agent or have reacted therewith, in the case of a pre-formed interparticle crosslinked aggregate. This time required for penetration is influenced by the thickness of the physically associated particles or the interparticle crosslinked aggregate, the particular plasticizer, and the amount of water in the plasticizing solution. The time for penetration tends to decrease with decreasing thickness of the aggregate, an increasing water concentration, increasing plasticizer hydrophilicity, and/or decreasing plasticizer molecular size. The time for penetration generally ranges from a few seconds to up to one hour. For an aggregate in sheet form having a thickness of less than about 2–3 mm, the time for penetration is typically from about 10 seconds to about 6 minutes. Solutions containing over about 60% plasticizer may require several minutes. In one embodiment in which an aqueous 60–80% glycerol solution is applied to the aggregate at an addition level to provide at least about 0.45 g glycerol/g dry aggregate, the plasticization time is about 3–40 minutes.

The flexible macrostructures as incorporated into disposable absorbent articles will not become brittle or stiff or crack and/or break in foreseeable storage or use conditions. Thus, the improved macrostructures provide absorbent efficacy via reduced fracture. More specifically, the capillary continuity of the interparticle crosslinked aggregate is maintained allowing full utilization of the macrostructure. In addition, the resilience of the flexible macrostructure tends to improve the comfort of the wearer of the absorbent article.

In use, liquids that are deposited onto or come in contact with the flexible macrostructures are imbibed by the precursor particles comprising the interparticle crosslinked aggregate of the macrostructure or are passed into the pores and transmitted to other portions of the macrostructure where they are imbibed by other precursor particles or transported through the macrostructure to other absorbent members adjacent thereto.

3. Applications

The flexible, porous, absorbent, polymeric macrostructures can be used for many purposes in many fields of use. For example, the macrostructures can be used for packing containers; drug delivery devices; wound cleaning devices; burn treatment devices; ion exchange column materials; construction materials; agricultural or horticultural materials such as seed sheets or water-retentive materials; and industrial uses such as sludge or oil dewatering agents, materials for the prevention of dew formation, dessicants, and humidity control materials.

The flexible, porous, absorbent, polymeric macrostructures of the present invention are useful when joined to a carrier. Carriers useful in the present invention include absorbent materials such as cellulose fibers. The carriers also may be any other carriers as are known in the art such as nonwoven webs, tissue webs, foams, polyacrylate fibers, apertured polymeric webs, synthetic fibers, metallic foils, elastomers, and the like. The macrostructures may be joined directly or indirectly to the carriers and may be joined thereto via chemical or physical bonding such as are known including adhesives or chemicals that react to adhere the macrostructures to the carriers.

Because of the unique absorbent properties of the flexible macrostructures of the present invention, the macrostructures are especially suitable for use as absorbent cores in absorbent articles, especially disposable absorbent articles. As used herein, the term "absorbent article" refers to articles which absorb and contain body exudates and more specifically refers to articles which are placed against or in proximity to the body of the wearer to absorb and contain the various exudates discharged from the body.

Figure 4:
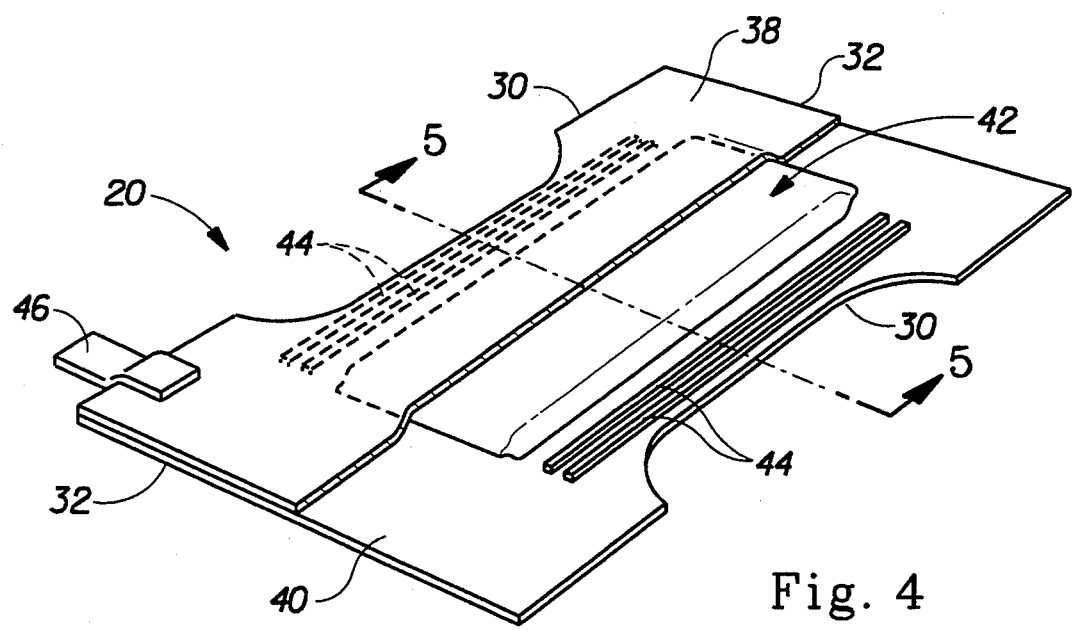
FIG. 4 is a perspective view of a disposable diaper embodiment of the present invention wherein portions of the topsheet have been cut-away to more clearly show the underlying absorbent core (an embodiment of an absorbent member of the present invention) of the diaper wherein the absorbent member comprises a flexible, porous, absorbent, polymeric macrostructure of the present invention.

A preferred embodiment of a disposable absorbent article, diaper 20, is shown in FIG. 4. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, sanitary napkins, facial tissues, paper towels, and the like.

FIG. 4 is a perspective view of the diaper 20 of the present invention in its uncontracted state (i.e., with all the elastic induced contraction removed) with portions of the structure being cut-away to more clearly show the construction of the diaper 20 and with the portion of the diaper 20 which contacts the wearer facing the viewer. The diaper 20 is shown in FIG. 4 to preferably comprise a liquid pervious topsheet 38; a liquid impervious backsheet 40 joined with the topsheet 38; an absorbent core 42 positioned between the topsheet 38 and the backsheet 40; elastic members 44; and tape tab fasteners 46. While the topsheet 38, the backsheet 40, the absorbent core 42, and the elastic members 44 may be assembled in a variety of well known configurations, preferred diaper configurations are described generally in U.S. Pat. No. 3,860,003 issued to Buell on Jan. 14, 1975; and U.S. Pat. No. 5,151,092 issued to Buell et al. on Sep. 29, 1992; each incorporated herein by reference. Alternatively preferred configurations for disposable diapers herein are also disclosed in U.S. Pat. No. 4,808,178 issued to Aziz and Blaney on Feb. 28, 1989; U.S. Pat. No. 4,695,278 issued to Lawson on Sep. 22, 1987; and U.S. Pat. No. 4,816,025 issued to Foreman on Mar. 28, 1989. These patents are incorporated herein by reference.

FIG. 4 shows a preferred embodiment of the diaper 20 in which the topsheet 38 and the backsheet 40 are co-extensive and have length and width dimensions generally larger than those of the absorbent core 42. The topsheet 38 is joined with and superimposed on the backsheet 40 thereby forming the periphery of the diaper 20. The periphery defines the outer perimeter or the edges of the diaper 20. The periphery comprises the end edges 32 and the longitudinal edges 30.

The topsheet 38 is compliant, soft feeling, and non-irritating to the wearer's skin. Further, the topsheet 38 is liquid pervious permitting liquids to readily penetrate through its thickness. A suitable topsheet 38 may be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. The topsheet 38 may be made of a hydrophobic material to isolate the wearers skin from liquids in the absorbent core 42. An exemplary topsheet 38 comprises staple length (i.e., having a length of at least about 15.9 mm (0.62 inches)) polypropylene fibers having a denier of about 1.5, such as Hercules type 151 polypropylene marketed by Hercules, Inc. of Wilmington, Del.

There are a number of manufacturing techniques which may be used to manufacture the topsheet 38. For example, the topsheet 38 may be woven, nonwoven, spunbonded, carded, or the like. A preferred topsheet is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction, and a wet tensile strength of at least about 55 grams per centimeter in the cross-machine direction.

The backsheet 40 is impervious to liquids and is preferably manufactured from a thin plastic film, although other flexible liquid impervious materials may also be used. The backsheet 40 prevents the exudates absorbed and contained in the absorbent core 42 from wetting articles which contact the diaper 20 such as bedsheets and undergarments. The backsheet 40 may permit vapors to escape from the absorbent core 42 while still preventing exudates from passing through the backsheet. A preferrred backsheet 40 is polyethylene film having a thickness from about 0.012 mm (0.5 mil) to about 0.051 centimeters (2.0 mils), although other flexible, liquid impervious materials may be used. As used herein, the term "flexible" refers to materials which are compliant and which will readily conform to the general shape and contours of the wearer's body. The backsheet 40 may be embossed and/or matte finished to provide a more clothlike appearance.

The size of the backsheet 40 is dictated by the size of the absorbent core 42 and the exact diaper design selected. In a preferred embodiment, the backsheet 40 has a modified hourglass-shape extending beyond the absorbent core 42 a minimum distance of at least about 1.3 centimeters to about 2.5 centimeters (about 0.5 to about 1.0 inch) around the entire diaper periphery.

The topsheet 38 and the backsheet 40 are joined together in any suitable manner. As used herein, the term "joined" encompasses configurations whereby the topsheet 38 is directly joined to the backsheet 40 by affixing the topsheet 38 directly to the backsheet 40, and configurations whereby the topsheet 38 is indirectly joined to the backsheet 40 by affixing the topsheet 38 to intermediate members which in turn are affixed to the backsheet 40. In a preferred embodiment, the topsheet 38 and the backsheet 40 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive may be used to affix the topsheet 38 to the backsheet 40.

Tape tab fasteners 46 are typically applied to the back waistband region of the diaper 20 to provide a fastening means for holding the diaper on the wearer. The tape tab fasteners 46 can be any of those well known in the art, such as the fastening tape disclosed in U.S. Pat. No. 3.848,594 issued to Kenneth B. Buell on Nov. 19, 1974, which patent is incorporated herein by reference. These tape tab fasteners 46 or other diaper fastening means are typically applied near the comers of the diaper 20. Alternative fastening systems suitable for use herein are disclosed in U.S. Pat. Nos. 4.846,815 (Scripps; Jul. 11, 1989); 4,894,060 (Nestegard; Jan. 16, 1990); 4,946,527 (Battrell; Aug. 7, 1990); B1 4,662,875 (Hirotsu et al.; May 5, 1987); and 5,151,092 (Buell et al.; Sep. 29, 1992); each being incorporated herein by reference.

The elastic members 44 are disposed adjacent the periphery of the diaper 20, preferably along each longitudinal edge 30, so that the elastic members 44 tend to draw and hold the diaper 20 against the legs of the wearer. Alternatively, the elastic members 44 may be disposed adjacent either or both of the end edges 32 of the diaper 20 to provide a waistband as well as or rather than leg cuffs. For example, a suitable waistband is disclosed in U.S. Pat. No. 4,515,595 issued to Kievit and Osterhage on May 7, 1985, incorporated herein by reference. In addition, a method and apparatus suitable for manufacturing a disposable diaper having elastically contractible elastic members is described in U.S. Pat. No. 4,081,301 issued to Buell on Mar. 28, 1978, incorporated herein by reference. Another suitable elastic waist feature is disclosed in the above referenced U.S. Pat. No. 5, 191,092 to Buell et al.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition, for example, by stretching and securing while the diaper 20 is in an uncontracted condition, or by contracting the diaper 20, e.g., by pleating, and securing the elastic members 44 to the diaper 20 while the elastic members 44 are in their unrelaxed or unstretched condition.

In the embodiment illustrated in FIG. 4, the elastic members 44 extend along a portion of the length of the diaper 20. Alternatively, the elastic members 44 may extend the entire length of the diaper 20, or any other length suitable to provide an elastically contractible line. The length of the elastic members 44 is dictated by the diaper design.

The elastic members 44 may take a multitude of configurations, including widths, single or multiple strands, or rectangular or curvilinear. Still further, the elastic members 44 may be affixed to the diaper in any of several ways which are known in the art, e.g., ultrasonically bonded, heat and pressure sealed or glued.

The absorbent core 42 of the diaper 20 is positioned between the topsheet 38 and the backsheet 40. The absorbent core 42 may be manufactured in a wide variety of sizes and shapes (e.g., rectangular, hourglass, asymmetrical, etc.) and from a wide variety of materials as are known in the art. The total absorbent capacity of the absorbent core 42 should, however, be compatible with the design liquid loading for the intended use of the absorbent article or diaper. Further, the size and absorbent capacity of the absorbent core 42 may vary to accommodate wearers ranging from infants through adults.

Figure 5:
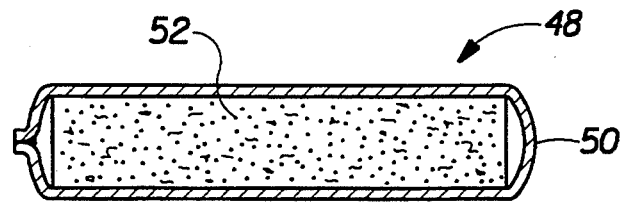
FIG. 5 is a cross-sectional view of the absorbent core of the diaper shown in FIG. 4 taken along sectional line 5—5 of FIG. 4.

The absorbent core 42 comprises the flexible porous, absorbent, polymeric macrostructures of the present invention. As shown in FIG. 5, the absorbent core 42 comprises an absorbent member 48 comprising an envelope web 50 and a porous, absorbent, polymeric macrostructure 52 disposed in the envelope web 50. As shown in FIG. 5, the macrostructure 52 is encased in an envelope web 50 to minimize the potential for the precursor particles to migrate through the topsheet and to provide an additional liquid transport layer between the topsheet 38 and the macrostructure 52 to enhance liquid acquisition and minimize rewet. The envelope web 50 may comprise a number of materials including nonwoven webs, paper webs, or webs of absorbent materials such as tissue paper. The envelope web 50 preferably comprises a nonwoven web similar to the webs used to form the topsheet 38 and is preferably hydrophilic to allow liquids to rapidly pass through the envelope web 50. Similar layered absorbent members (laminates) are more fully described in U.S. Pat. No. 4,578,068 issued to Kramer et al. on Mar. 25, 1986; incorporated herein by reference.

Alternatively, the absorbent cores 42 of the present invention may consist solely of one or more (a multiplicity of the) flexible, porous, absorbent, polymeric macrostructures of the present invention; may comprise a combination of layers including the flexible macrostructures of the present invention; or any other absorbent core configurations including one or more of the flexible macrostructures of the present invention. The flexible, porous, absorbent, polymeric macrostructures may be slitted and incorporated in the absorbent core 42 as described in commonly assigned U.S. patent application Ser. Nos. 142,253, filed in the names of Hsueh et al. on Oct. 22, 1993; 142,259, filed in the names of Rezai et al. on Oct. 22, 1993; and 142,629, filed in the names of Dierckes et al. on Oct. 22, 1993; each being incorporated herein by reference.

Figure 6:
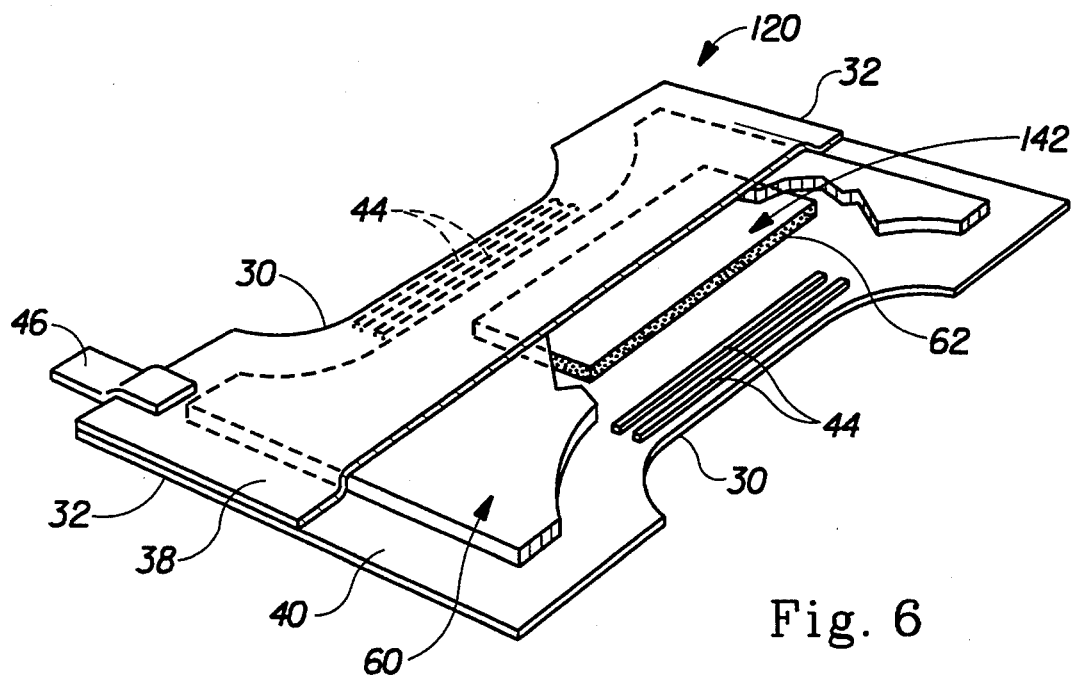
FIG. 6 is a perspective view of a disposable diaper embodiment of the present invention wherein portions of the topsheet have been cut away to more clearly show an alternative absorbent core embodiment.

FIG. 6 shows an alternative embodiment of the diaper 120 comprising a dual-layer absorbent core 142 comprising a modified hourglass-shaped absorbent member 60 and a sheet 62 of the flexible, porous, absorbent, polymeric macrostructure positioned subjacent the absorbent member 60 (i.e., between the absorbent member 60 and the backsheet 40).

The absorbent member 60 serves to quickly collect and temporarily hold discharged liquids and to transport such liquids by wicking from the point of initial contact to other parts of the absorbent member 60 and to the macrostructure sheet 62. The absorbent member 60 preferably comprises a web or batt of fiber materials. Various types of fiber material as are known in the art can be used in the absorbent member 60. Cellulosic fibers are generally preferred for use herein, wood pulp fibers being especially preferred. The absorbent member 60 can also contain a particulate, absorbent, polymeric composition, for example the polymeric materials described herein in reference to the precursor particles, provided that such inclusion does not substantially interfere with the collection and transport of liquids through the absorbent member and to the flexible macrostructure sheet. The absorbent member 60 may also comprise chemically stiffened cellulosic fibers as previously discussed herein. Exemplary embodiments of the absorbent member 60 useful in the present invention are described in U.S. Pat. No. 4,673,402 issued to Weisman et al. on Jun. 16, 1987; and U.S. Pat. No. 4,834,735 issued to Alemany et al on May 30, 1989; each incorporated herein by reference.

The absorbent member 60 can be of any desired shape, for example, rectangular, oval, oblong, asymmetric or hourglass-shaped. The shape of the absorbent member 60 may define the general shape of the resulting diaper 120. As shown in FIG. 6 the absorbent member 60 is hourglass-shaped.

The flexible macrostructure sheet 62 of the present invention need not be the same size as the absorbent member 60 and can, in fact, have a top surface which is substantially smaller or larger than the top surface area of the absorbent member 60. As shown in FIG. 6 the flexible macrostructure sheet 62 is smaller than the absorbent member 60 and has a top surface area from about 0.10 to about 1.0 times that of the absorbent member 60. In an alternative embodiment, the absorbent member 60 is smaller than the flexible macrostructure sheet 62 and has a top surface area from about 0.25 to about 1.0 times that of the absorbent member 60. In this alternative embodiment, the absorbent member 60 preferably comprises chemically stiffened cellulosic fibers.

The flexible macrostructure sheet 62 is preferably placed in a specific positional relationship with respect to the backsheet 40 and/or the absorbent member 60 in the diaper. More particularly, the flexible macrostructure sheet 62 is positioned generally toward the front of the diaper so that the flexible macrostructure sheet 62 is most effectively located to acquire and hold discharged liquids.

In alternatively preferred embodiments, a multiplicity of flexible macrostructures, e.g., from about two to about six macrostructure strips or sheets, may be substituted for the single flexible macrostructure sheet 62 shown in FIG. 6. Further, additional absorbent layers, members, or structures may be placed into the absorbent core 142. For example, an additional absorbent member may be positioned between the flexible macrostructure sheet 62 and the backsheet 40 to provide reserve capacity for the absorbent core 142 and/or a layer to distribute liquids passing through the flexible macrostructure sheet 62 to other portions of the absorbent core 142 or to the macrostructure sheet 62. The flexible macrostructure sheet 62 may also alternatively be positioned over the absorbent member 60 so as to be positioned between the topsheet 38 and the absorbent member 60.

In use, the diaper 20 is applied to a wearer by positioning the back waistband region under the wearer's back, and drawing the reminder of the diaper 20 between the wearers legs so that the front waistband region is positioned across the front of the wearer. The tape-tab fasteners 46 are then secured preferably to outwardly facing areas of the diaper 20. In use, disposable diapers or other absorbent articles incorporating the flexible, porous, absorbent, polymeric macrostructures of the present invention tend to more quickly and efficiently distribute and store liquids and to remain dry due to the high absorbent capacity of the flexible macrostructures.

4. Examples.

A) Plasticization of Pre-formed Interparticle Crosslinked Aggregate (i) Preparation of Interparticle Crosslinked Aggregate An interparticle crosslinked aggregate is prepared in accordance with Example 1 of U.S. Pat. No. 5,102,597 issued to Roe et al. on Apr. 7, 1992. The aggregate comprises 350 grams of precursor particles of slightly network crosslinked, partially neutralized poly (acrylic acid) having a particle size of from 150–250 microns. The interparticle crosslinking agent (glycerol) is contained in a solution additionally containing methanol and water. The solution comprises 7 g glycerol, 35 g methanol, and 7 g water. The precursor particles are mixed in a Kitchen Aid Mixer KS55 while the crosslinking solution is applied via a Pre-Val sprayer. The resultant mixture is compacted via a screw extruder with compaction rolls having shims set at 0.055". The interparticle crosslinking agent is then reacted with the polymer of the precursor particles by subjecting the compacted mixture to a temperature of 210° C. in a standard laboratory oven for a period of 45 minutes to form the interparticle crosslinked aggregate. The finished thickness of the resultant sheet, hereinafter referred to as Sheet A, is about 0.03".

B) Preparation of the Flexible, Porous, Absorbent Polymeric Macrostructure (Ex. 1) 0.72 g of a plasticizing solution formed of 40.41 g glycerol and 10.16 g water is sprayed evenly on both sides of a 1.19 g sample of the Sheet A in two applications. In the first application, 0.41 g of the solution is applied. After 4 minutes, 0.31 g is applied. All of the applied solution was absorbed within 15 minutes.

(Ex. 2) 1.22 g of a plasticizing solution formed of 31.86 g glycerol and 14.02 g water is sprayed evenly on both sides of a 1.27 g sample of the Sheet A in two applications. In the first application 0.46 g of the solution is applied. After 1.5 minutes, 0.76 g of the solution is applied. All of the solution is absorbed into the sample within 5.5 minutes of initial solution contact.

(Ex. 3) 0.93 g of a plasticizing solution formed of 40.41 g glycerol and 10.16 g water is sprayed evenly on both sides of a 1.07 g sample of the Sheet A in two applications as follows: 0.54 g; then after 5 minutes 0.39 g. About 20–40 minutes was required for complete absorption. The sample was initially stiff but was resilient after complete absorption.

(Ex. 4) 2.07 g of a plasticizing solution as in Example 1 is sprayed on both sides of a 1.39 g sample of Sheet A in three applications as follows: 0.53 g; then after 1 minute 0.74 g; then after 2 additional minutes 0.80 grams. All of the solution is absorbed within a total of five minutes.

(Ex. 5) 1.72 grams of a plasticizing solution formed of 59.9 g ethylene glycol and 30.41 g water is sprayed evenly on both sides of a 2.05 g sample of the Sheet A in three applications. At least about 5 minutes were required for complete absorption of the solution.

(Ex. 6) 1.93 g of a plasticizing solution formed of 28 g ethylene glycol and 12.02 g water is sprayed evenly on both sides of a 1.62 g sample of the Sheet A in three applications as follows: 0.45 g; then after 3 minutes 1.08 g; then after 1 additional minute 0.40 g. A total of about 6 minutes was required for complete absorption of the solution.

Comparative Examples (CE-1) A 1.59 g sample of Sheet A was placed in an 80° F./80% R. H. room until the sample weighed 2.77 g, indicating absorption of 1.18 g of water from the environment.

(CE-2) 0.45 g of a plasticizing solution formed of 25.26 g glycerol and 37.63 g water is sprayed evenly on both sides of a 0.45 g sample of the Sheet A in one application.

(CE-3) 0.81 g of a plasticizing solution formed of 59.9 g ethylene glycol and 30.41 g water is sprayed evenly on both sides of a 2.17 g sample of the Sheet A in one application. At least about 5 minutes were required for complete absorption of the solution.

(CE-4) 0.48 g of a plasticizing solution formed of 58.20 g ethylene glycol and 58.27 g water is sprayed evenly on both sides of a 0.77 g sample of the Sheet A in one application.

(CE-5) 1.09 g of a plasticizing solution formed of 18.02 g ethylene glycol and 32.45 g water is sprayed evenly on both sides of a 1.01 g sample of the Sheet A in one application.

(CE-6) 1.90 g of a plasticizing solution formed of 20.30 g ethylene glycol and 37.8 g water is sprayed evenly on both sides of a 0.96 g sample of the Sheet A in one application.

(CE-7) 0.69 g of a plasticizing solution formed of 35.09 g of 1,2-propane diol and 15.46 g water is sprayed evenly on both sides of a 1.26 g sample of the Sheet A in three applications as follows: 0.44 g; then after 2 minutes 0.12 g; then after 4.5 additional minutes 0.13 g. Slightly more than 8 minutes was required for complete absorption of the solution.

Test Method—Flexibility by Bending Angle at Cracking or Breaking

Figure 7:
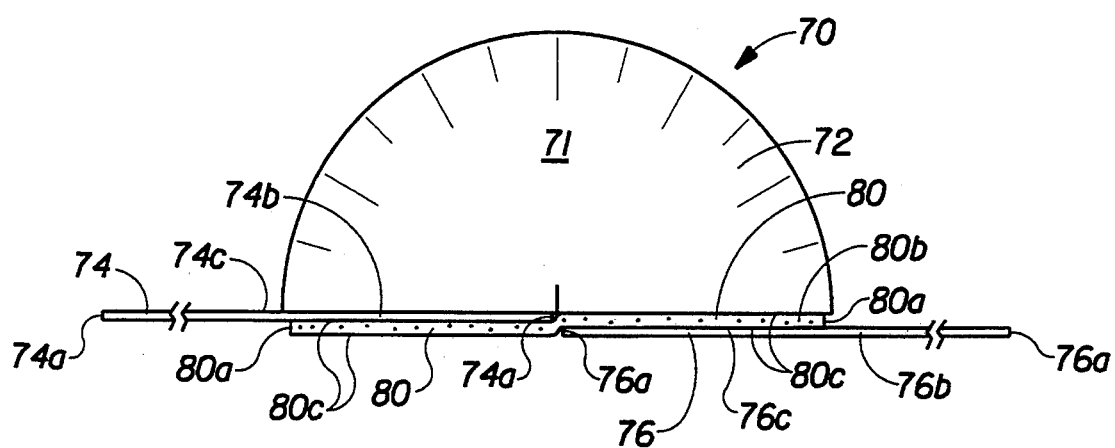
FIG. 7 is an apparatus for determining the flexibility of the flexible macrostructures of the present invention.

FIG. 7 shows a suitable apparatus 70 for determining the flexibility of the flexible macrostructures of the present invention. The apparatus 70 has a protractor 72 having a face 71 having angular markings, a longitudinal straight edge (not shown), an origin positioned at the midpoint of the straight edge (not shown); a first rectangular ruler 74 having end edges 74a connected by two parallel spaced apart longitudinal edges 74b defining planar surfaces 74c; and a second rectangular ruler 76 having end edges 76a connected by two parallel spaced apart longitudinal edges 76b defining planar surfaces 76c. The ruler 74 and ruler 76 are positioned adjacent to the face 71 of the protractor 72 substantially along the straight edge such that the planar surfaces 74c and 76c are perpendicular to the face 71 of the protractor 72. FIG. 7 also shows a Sample 80 of a flexible macrostructure of the present invention having end edges 80a connected by two parallel spaced longitudinal edges 80b defining planar surfaces 80c, Sample 80 is positioned between the ruler 74 and ruler 76, with the longitudinal midpoint of the Sample 80 being positioned at the origin of the protractor 72, with the longitudinal edges 74b, 76b and 80b being aligned as shown.

A protractor 72 having a suitable size, e.g., having a 3″ radius, is affixed to a stable horizontal support surface with its straight edge positioned on the surface such that the face 71 of the protractor showing the various angular degrees is in an upright 90° vertical position relative to the support surface. A 141 wide (1″ end edges 76a), 12″ long (12″ longitudinal edges), approximately 1 mm thick metal ruler 76 is positioned on the support surface with one longitudinal edge 76b immediately adjacent the straight edge of the protractor 72 (the surface 76c flat on the support surface and perpendicular to the face 71 of the protractor 72), with one end edge 76a of the ruler 76 being positioned at the origin of the protractor 72 (i.e., the midpoint of the straight edge of the protractor 72, which corresponds to the 90° line of the protractor 72) such that the ruler 76 extends to the right of the origin.

The Sample 80 in a flat, unfolded or otherwise undeformed configuration is then positioned on top of the ruler 76, with a longitudinal edge of the Sample 80 being positioned substantially immediately adjacent to the straight edge of the protractor 72 (the surface 80c being perpendicular to the face 71 of the protractor 72) such that the longitudinal edges of the Sample 80 and the ruler 76 are registered, and the longitudinal midpoint of the Sample 80 being positioned at the origin of the protractor 72.

Another 1″ wide (1″ end edges 74a), 12″ long (12″ longitudinal edges), approximately 1 mm thick metal ruler 74 is positioned on top of the Sample 80 and affixed to firmly hold the Sample 80 without cutting into the Sample 80 or otherwise substantially compressing or deforming the Sample 80. The second ruler 74 is positioned with a longitudinal edge 74b substantially immediately adjacent the straight edge of the protractor 72 (the surface 74c being perpendicular to the face 71 of the protractor 72) such that the longitudinal edges 74b and 80b of the ruler 74 and the Sample 80 are aligned as shown, with one end edge 74a of the ruler 74 being positioned at the origin of the protractor 72 such that the ruler 74 extends to the left of the origin, The flexibility of an interparticle crosslinked aggregate or of the flexible macrostructures of the present invention comprising an interparticle crosslinked aggregate is determined in the following manner. A 1″ wide (1″ end edges 80a) ×6″ long (6″ longitudinal edges 80b)×2-3 mm thick Sample 80 of the aggregate/macrostructure is conditioned in a 120° F.±5° F./8%±2% Relative Humidity environment. The flexibility of the Sample 80 is checked periodically by determining the bending angle at cracking or breaking as follows after exposure to these conditions over extended time periods. The Sample is held in the 120° F.±5° F./8%±2% Relative Humidity environment during testing. The Sample 80 is then bent across its width around the end edge 74a of the ruler 74 in the upward direction. The Sample 80 is bent by elevating the outboard end edge 76a opposite the end edge 76a positioned at the origin of the protractor 72 at a rate of about 15 angular degrees per second.

The surface 76c of the ruler 76 and thereby the surface 80c of the Sample 80 are kept in perpendicular position to the face 71 of the protractor 72 while elevating the end edge 76a so that the Sample 80 is articulated about the origin of the protractor 72. The ruler 76 provides even support of the portion of the Sample 80 that is being upwardly bent, while the ruler 74 serves to hold the other portion of the Sample 80 in a stationary position. Pinching of the Sample 80 between the end edges 74a and 76a of the ruler 74 and ruler 76, respectively, is minimized. The Sample 80 is bent until cracking or breaking is first visually observed without magnification or tactilely discerned. Cracking or breaking is shown by a marked discontinuity in the capillary channels of the Sample 80 along at least a portion of the width of the Sample 80. Cracking involves discontinuities through pad of the thickness of the Sample 80; breaking involves complete severance of the Sample 80 through its thickness. Such cracking or breaking along the capillary channels interferes with the capillary transport of fluids by the aggregate/macrostructure.

The angle corresponding to the point at which such cracking or breaking occurs is noted as the bending angle at cracking or breaking after a given time period in the environment. The time in the environment for cracking or breaking at a 90° bending angle is noted. The flexibility for the above examples and comparative examples as determined by bending angle is shown in Table 1.

TABLE 1

| example | type plasticizer (P) | wt. % P in aqueous plasticizing solution | parts P/ parts aggregate by wt. | time to crack/break at 90° bending angle |
|---|---|---|---|---|
| 1 | glycerol | 79.9 | 0.48 | >28 days |
| 2 | glycerol | 69.4 | 0.67 | >35 days |
| 3 | glycerol | 79.9 | 0.69 | >28 days |
| 4 | glycerol | 69.4 | 1.03 | >28 days |
| 5 | ethylene glycol | 66.3 | 0.56 | 4.6 hrs (276 min) |
| 6 | ethylene glycol | 70 | 0.83 | >5 hours |
| CE-1 | water | 0 | 0 | <70 min |
| CE-2 | glycerol | 40.2 | 0.40 | >70 min; <2 hrs |
| CE-3 | ethylene glycol | 66.3 | 0.25 | 2 hours |
| CE-4 | ethylene glycol | 50 | 0.31 | <2.6 hrs (154 min) |
| CE-5 | ethylene glycol | 35.7 | 0.39 | <30 min |
| CE-6 | ethylene glycol | 35 | 0.69 | 2 hrs |
| CE-7 | 1,2-propane dioll | 69.4 | 0.38 | <60 min |

As shown by Table 1, macrostructures having 0.40 or less parts by weight of plasticizer to 1 part by weight of the unplasticized aggregate lost flexibility within a period of 3 hours or less in the 120° F.±5° F./8%±2% Relative Humidity environment as measured by bending angle. Macrostructures having greater than 0.45 parts by weight of plasticizer to 1 part by weight of the unplasticized aggregate remained flexible for periods greater than about 4 hours in the environment, with some retaining flexibility for more than 28 days in the environment.

As also shown by Table 1, at least 40% plasticizer is needed in the plasticizing solution in order to achieve the noted flexibilities. In addition, the time for absorption increases with increasing solution plasticizer concentration. A plasticizing solution containing from about 60–80% plasticizer provides the best balance of flexibility and absorption time.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A flexible, porous, absorbent, polymeric macrostructure formed by a process comprising the steps of:
   (a) providing a multiplicity of precursor particles of substantially water-insoluble, absorbent, hydrogel-forming, polymer material;
   (b) applying an interparticle crosslinking agent onto said precursor particles, said interparticle crosslinking agent being capable of reacting with said polymer material of said precursor particles;
   (c) physically associating said precursor particles to form an aggregate having pores interconnected by intercommunicating channels;
   (d) reacting said interparticle crosslinking agent with said polymer material of said precursor particles of said aggregate, while maintaining said physical association of said precursor particles, to form crosslink bonds between said precursor particles to form an interparticle crosslinked aggregate having pores interconnected by intercommunicating channels; and
   (e) applying a plasticizing solution comprising at least about 40% by weight of a plasticizer and less than about 60% by weight water, based on the total weight of said solution, to said interparticle crosslinked aggregate at a loading of at least about 0.45 part by weight of said plasticizer to 1 part by weight of said precursor particles, said plasticizer being a water-soluble, organic polyhydroxy compound.

2. The macrostructure of claim 1 wherein said plasticizing solution comprises at least about 50% by weight of said plasticizer and less than about 50% by weight of said water, based on the total weight of said solution.

3. The macrostructure of claim 2 wherein said plasticizing solution comprises at least about 60% by weight of said plasticizer and less than about 40% by weight of said water, based on the total weight of said solution.

4. The macrostructure of claim 3 wherein said plasticizing solution comprises from about 60% to about 80% by weight of said plasticizer and from about 40% to about 20% by weight of said water, based on the total weight of said solution.

5. The macrostructure of claim 1 wherein said plasticizing solution is applied to said interparticle crosslinked aggregate at a loading of at least about 0.5 part by weight of said plasticizer to 1 part by weight of said precursor particles.

6. The macrostructure of claim 5 wherein said plasticizing solution is applied to said interparticle crosslinked aggregate at a loading of at least about 0.6 part by weight of said plasticizer to 1 part by weight of said precursor particles.

7. The macrostructure of claim 1 wherein said plasticizer is selected from the group consisting of glycerol; 1,2-propane diol; 1,3-propanediol; ethylene glycol; sorbitol; sucrose; polymeric solutions comprising polyvinyl alcohol, ester precursors of polyvinyl alcohol, or polyethylene glycol; polyglycerols having a weight average molecular weight of from about 150 to about 800; polyoxyethylene glycols having a weight average molecular weight of from about 200 to about 400; polyoxypropylene glycols having a weight average molecular weight of from about 200 to about 400; and mixtures thereof.

8. The macrostructure of claim 7 wherein said plasticizer is selected from the group consisting of glycerol, ethylene glycol, 1,2-propane diol, 1,3-propane diol, and mixtures thereof.

9. The macrostructure of claim 8 wherein said plasticizer is glycerol.

10. The macrostructure of claim 1 wherein said polymer material of said precursor particles is selected from the group consisting of hydrolyzed starch-acrylonitrile graft copolymer; partially neutralized starch-acrylonitrile graft copolymer; starch-acrylic acid graft copolymer; partially neutralized starch-acrylic acid graft copolymer; saponified vinyl acetate-acrylic ester copolymers; hydrolyzed acrylonitrile or acrylamide copolymers; slightly network crosslinked products of any of the foregoing copolymers; partially neutralized polyacrylic acid; or slightly network crosslinked products of partially neutralized polyacrylic acid; and said interparticle crosslinking agent is selected from the group consisting of polyhydric alcohol compounds, polyglycidyl ether compounds, polyfunctional aziridine compounds, polyfunctional amine compounds, and polyfunctional isocyanate compounds.

11. The macrostructure of claim 10 wherein said polymer material of said precursor particles consists essentially of slightly network crosslinked products of partially neutralized polyacrylic acid; and said interparticle crosslinking agent is selected from the group consisting of ethylene glycol, glycerol, trimethylol propane, 1,2-propanediol, or 1,3-propanediol.

12. A flexible, porous, absorbent, polymeric macrostructure formed by a process comprising the steps of:
   (a) providing a multiplicity of precursor particles of substantially water-insoluble, absorbent, hydrogel-forming, polymer material;
   (b) applying an interparticle crosslinking agent onto said precursor particles, said interparticle crosslinking agent being capable of reacting with said polymer material of said precursor particles;
   (c) physically associating said precursor particles to form an aggregate having pores interconnected by intercommunicating channels;
   (d) reacting said interparticle crosslinking agent with said polymer material of said precursor particles of said aggregate, while maintaining said physical association of said precursor particles, to form crosslink bonds between said precursor particles to form an interparticle crosslinked aggregate having pores interconnected by intercommunicating channels; and
   (e) applying a plasticizing solution comprising at least about 50% by weight of a plasticizer and less than about 50% by weight water, based on the total weight of said solution, to said interparticle crosslinked aggregate at a loading of at least about 0.45 part by weight of said plasticizer to 1 part by weight of said precursor particles, said plasticizer being selected from the group consisting of glycerol; 1,2-propane diol; 1,3-propanediol; ethylene glycol; sorbitol; sucrose; polymeric solutions comprising polyvinyl alcohol, ester precursors of polyvinyl alcohol, or polyethylene glycol; polyglycerols having a weight average molecular weight of from about 150 to about 800; polyoxyethylene glycols having a weight average molecular weight of from about 200 to about 400; polyoxypropylene glycols having a weight average molecular weight of from about 200 to about 400; and mixtures thereof.

13. The macrostructure of claim 12 wherein said plasticizing solution comprises at least about 60% by weight of said plasticizer and less than about 40% by weight of said water, based on the total weight of said solution.

14. The macrostructure of claim 13 wherein said plasticizing solution comprises from about 60% to about 80% by weight of said plasticizer and from about 40% to about 20% by weight of said water, based on the total weight of said solution.

15. The macrostructure of claim 12 wherein said plasticizing solution is applied to said interparticle crosslinked aggregate at a loading of at least about 0.5 part by weight of said plasticizer to 1 part by weight of said precursor particles.

16. The macrostructure of claim 15 wherein said plasticizing solution is applied to said interparticle crosslinked aggregate at a loading of at least about 0.6 part by weight of said plasticizer to 1 part by weight of said precursor particles.

17. The macrostructure of claim 12 wherein said plasticizer is selected from the group consisting of glycerol, ethylene glycol, 1,2-propane diol, 1,3-propane diol, and mixtures thereof.

18. The macrostructure of claim 1 wherein the macrostructure has a bending angle at cracking or breaking of at least 90° after being subjected to conditions of 120° F. ±5° F. and 8%±2% Relative Humidity for a period of at least about 4 hours.

19. The macrostructure of claim 18 wherein the macrostructure has a bending angle at cracking or breaking of at least 90° after being subjected to conditions of 120° F. ±5° F. and 8%±2% Relative Humidity for a period of at least about 24 hours.

20. The macrostructure of claim 19 wherein the macrostructure has a bending angle at cracking or breaking of at least 90° after being subjected to conditions of 120° F.±5° F. and 8%±2% Relative Humidity for a period of at least about 28 days.

* * * * *